US010286106B2

(12) United States Patent
Kahook et al.

(10) Patent No.: US 10,286,106 B2
(45) Date of Patent: *May 14, 2019

(54) INTRAOCULAR LENSES

(71) Applicant: The Regents of the University of Colorado, Denver, CO (US)

(72) Inventors: Malik Y. Kahook, Denver, CO (US); Naresh Mandava, Denver, CO (US); Robin Shandas, Boulder, CO (US); Bryan Rech, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,260

(22) Filed: May 17, 2016

(65) Prior Publication Data
US 2016/0256600 A1 Sep. 8, 2016

Related U.S. Application Data

(63) Continuation of application No. 14/026,832, filed on Sep. 13, 2013, now Pat. No. 9,427,493, which is a
(Continued)

(51) Int. Cl.
*A61L 27/16* (2006.01)
*A61L 27/50* (2006.01)
(Continued)

(52) U.S. Cl.
CPC .............. *A61L 27/16* (2013.01); *A61F 2/16* (2013.01); *A61F 2/1659* (2013.01); *A61F 9/007* (2013.01);
(Continued)

(58) Field of Classification Search
USPC .................. 523/105; 623/6.58, 6.6; 524/916; 525/226
See application file for complete search history.

(56) References Cited

U.S. PATENT DOCUMENTS

| 4,253,200 A | 3/1981 | Kelman |
| 4,494,954 A | 1/1985 | Suminoe et al. |

(Continued)

FOREIGN PATENT DOCUMENTS

| CA | 2527976 A1 | 12/2004 |
| DE | 10334108 A1 | 2/2005 |

(Continued)

OTHER PUBLICATIONS

Author Unknown, "0.018" and 0.035" Fibered Platinum Coils," Boston Scientific Corporation, 2010, 1 page.
(Continued)

*Primary Examiner* — Tae H Yoon
(74) *Attorney, Agent, or Firm* — Johnson & Johnson Surgical Vision, Inc.

(57) ABSTRACT

A shape memory polymer (SMP) intraocular lens may have a refractive index above 1.45, a Tg between 10° C. and 60° C., inclusive, de minimis or an absence of glistening, and substantially 100% transmissivity of light in the visible spectrum. The intraocular lens is then rolled at a temperature above Tg of the SMP material. The intraocular device is radially compressed within a die to a diameter of less than or equal to 1.8 mm while maintaining the temperature above Tg. The compressed intraocular lens device may be inserted through an incision less than 2 mm wide in a cornea or sclera or other anatomical structure. The lens can be inserted into the capsular bag, the ciliary sulcus, or other cavity through the incision. The SMP can substantially achieve refractive index values of greater than or equal to 1.45.

10 Claims, 16 Drawing Sheets

Related U.S. Application Data continuation-in-part of application No. 13/441,754, filed on Apr. 6, 2012, now Pat. No. 8,685,089, which is a continuation of application No. 13/500,884, filed as application No. PCT/US2012/028150 on Mar. 7, 2012, now abandoned.

(60) Provisional application No. 61/449,865, filed on Mar. 7, 2011, provisional application No. 61/474,696, filed on Apr. 12, 2011.

(51) Int. Cl.

| | | |
|---|---|---|
| *A61F 2/16* | (2006.01) | |
| *B29D 11/02* | (2006.01) | |
| *B29C 61/06* | (2006.01) | |
| *B29C 61/00* | (2006.01) | |
| *A61F 9/007* | (2006.01) | |
| *A61L 27/26* | (2006.01) | |
| *B29C 69/02* | (2006.01) | |
| *B29L 11/00* | (2006.01) | |
| *A61F 2/14* | (2006.01) | |
| *B29L 31/00* | (2006.01) | |

(52) U.S. Cl.
CPC .............. *A61L 27/26* (2013.01); *A61L 27/50* (2013.01); *B29C 61/003* (2013.01); *B29C 61/06* (2013.01); *B29C 69/025* (2013.01); *B29D 11/023* (2013.01); *A61F 2/14* (2013.01); *A61F 2/142* (2013.01); *A61F 2002/169* (2015.04); *A61F 2002/1683* (2013.01); *A61F 2002/1696* (2015.04); *A61F 2002/16965* (2015.04); *A61F 2002/169053* (2015.04); *A61F 2210/0014* (2013.01); *A61F 2240/001* (2013.01); *A61L 2400/16* (2013.01); *A61L 2430/16* (2013.01); *B29K 2995/0037* (2013.01); *B29L 2011/0016* (2013.01); *B29L 2031/7532* (2013.01)

(56) References Cited

U.S. PATENT DOCUMENTS

| | | |
|---|---|---|
| 4,528,311 A | 7/1985 | Beard et al. |
| 4,573,998 A | 3/1986 | Mazzocco |
| 4,594,401 A | 6/1986 | Takahashi et al. |
| 4,606,336 A | 8/1986 | Zeluff |
| 4,716,234 A | 12/1987 | Dunks et al. |
| 4,731,079 A | 3/1988 | Stoy |
| 4,813,957 A | 3/1989 | McDonald |
| 4,820,782 A | 4/1989 | Ueno |
| 4,889,664 A | 12/1989 | Kindt-Larsen et al. |
| 4,950,258 A | 8/1990 | Kawai et al. |
| 4,955,580 A | 9/1990 | Seden et al. |
| 4,994,069 A | 2/1991 | Ritchart et al. |
| 5,116,337 A | 5/1992 | Johnson |
| 5,163,952 A | 11/1992 | Froix |
| 5,192,303 A | 3/1993 | Gatturna et al. |
| 5,234,430 A | 8/1993 | Huebner |
| 5,258,020 A | 11/1993 | Froix |
| 5,331,073 A | 7/1994 | Weinschenk, III |
| 5,358,511 A | 10/1994 | Gatturna et al. |
| 5,391,168 A | 2/1995 | Sanders et al. |
| 5,395,374 A | 3/1995 | Miller et al. |
| 5,445,140 A | 8/1995 | Tovey |
| 5,450,842 A | 9/1995 | Tovey et al. |
| 5,505,735 A | 4/1996 | Li |
| 5,551,871 A | 9/1996 | Besselink et al. |
| 5,562,663 A | 10/1996 | Wisnewski et al. |
| 5,591,185 A | 1/1997 | Kilmer et al. |
| 5,599,291 A | 2/1997 | Balbierz et al. |
| 5,601,557 A | 2/1997 | Hayhurst |
| 5,603,722 A | 2/1997 | Phan et al. |
| 5,609,608 A | 3/1997 | Benett et al. |
| 5,674,241 A | 10/1997 | Bley et al. |
| 5,674,242 A | 10/1997 | Phan et al. |
| 5,702,402 A | 12/1997 | Brady |
| 5,728,098 A | 3/1998 | Sherman et al. |
| 5,762,630 A | 6/1998 | Bley et al. |
| 5,765,682 A | 6/1998 | Bley et al. |
| 5,797,911 A | 8/1998 | Sherman et al. |
| 5,866,635 A | 2/1999 | Collins et al. |
| 5,879,382 A | 3/1999 | Boneau |
| 5,899,938 A | 5/1999 | Sklar et al. |
| 5,911,737 A | 6/1999 | Lee et al. |
| 5,928,237 A | 7/1999 | Farris et al. |
| 5,961,520 A | 10/1999 | Beck, Jr. et al. |
| 5,964,744 A | 10/1999 | Balbierz et al. |
| 5,968,070 A | 10/1999 | Bley et al. |
| 5,976,187 A | 11/1999 | Richelsoph |
| 6,024,764 A | 2/2000 | Schroeppel |
| 6,053,944 A | 4/2000 | Tran et al. |
| 6,059,815 A | 5/2000 | Lee et al. |
| 6,077,268 A | 6/2000 | Farris et al. |
| 6,090,125 A | 7/2000 | Horton |
| 6,102,933 A | 8/2000 | Lee et al. |
| 6,160,084 A | 12/2000 | Langer et al. |
| 6,165,198 A | 12/2000 | McGurk et al. |
| 6,210,413 B1 | 4/2001 | Justis et al. |
| 6,235,028 B1 | 5/2001 | Brumfield et al. |
| 6,240,630 B1 | 6/2001 | Lee et al. |
| 6,241,691 B1 | 6/2001 | Ferrera et al. |
| 6,248,129 B1 | 6/2001 | Froix |
| 6,264,694 B1 | 7/2001 | Weiler |
| 6,281,262 B1 | 8/2001 | Shikinami |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,353,069 B1 | 3/2002 | Freeman et al. |
| 6,368,356 B1 | 4/2002 | Zhong et al. |
| 6,388,043 B1 | 5/2002 | Langer et al. |
| 6,500,204 B1 | 12/2002 | Igaki |
| 6,514,237 B1 | 2/2003 | Maseda |
| 6,514,257 B2 | 2/2003 | Dovesi et al. |
| 6,616,617 B1 | 9/2003 | Ferrera et al. |
| 6,620,195 B2 | 9/2003 | Goble et al. |
| 6,632,245 B2 | 10/2003 | Kim |
| 6,637,995 B1 | 10/2003 | White |
| 6,702,976 B2 | 3/2004 | Sokolowski |
| 6,712,810 B2 | 3/2004 | Harrington et al. |
| 6,720,402 B2 | 4/2004 | Langer et al. |
| 6,730,124 B2 | 5/2004 | Steiner |
| 6,740,094 B2 | 5/2004 | Maitland et al. |
| 6,746,461 B2 | 6/2004 | Fry |
| 6,780,899 B2 | 8/2004 | Liao et al. |
| 6,814,756 B1 | 11/2004 | Michelson |
| 6,887,266 B2 | 5/2005 | Williams et al. |
| 6,929,233 B2 | 8/2005 | Andino et al. |
| 6,935,743 B2 | 8/2005 | Shadduck |
| 7,115,691 B2 | 10/2006 | Alvarado et al. |
| 7,151,157 B2 | 12/2006 | Mather |
| 7,208,550 B2 | 4/2007 | Mather et al. |
| 7,217,744 B2 | 5/2007 | Lendlein et al. |
| 7,291,154 B2 | 11/2007 | Maitland et al. |
| 7,303,642 B2 | 12/2007 | Topolkaraev |
| 7,611,524 B1 | 11/2009 | Maitland et al. |
| 7,632,303 B1 | 12/2009 | Stalker et al. |
| 7,651,528 B2 | 1/2010 | Montgomery et al. |
| 7,699,893 B2 | 4/2010 | Donnelly et al. |
| 7,731,750 B2 | 6/2010 | Bojarski et al. |
| 7,794,476 B2 | 9/2010 | Wisnewski |
| 8,241,567 B2 | 8/2012 | Cai et al. |
| 8,377,120 B2 | 2/2013 | Lipshitz et al. |
| 8,685,089 B2 | 4/2014 | Kahook et al. |
| 9,062,141 B2 | 6/2015 | Goodrich et al. |
| 9,427,493 B2 * | 8/2016 | Kahook .................. A61F 2/16 |
| 2001/0018619 A1 | 8/2001 | Enzerink et al. |
| 2001/0041937 A1 | 11/2001 | Rieser et al. |
| 2002/0013586 A1 | 1/2002 | Justis et al. |
| 2002/0062547 A1 | 5/2002 | Chiodo et al. |
| 2002/0124857 A1 | 9/2002 | Schroeppel |
| 2002/0161371 A1 | 10/2002 | Bezemer et al. |

(56) References Cited

U.S. PATENT DOCUMENTS

| | | |
|---|---|---|
| 2002/0188298 A1 | 12/2002 | Chan |
| 2003/0055198 A1 | 3/2003 | Langer et al. |
| 2003/0066533 A1 | 4/2003 | Loy |
| 2003/0083735 A1 | 5/2003 | Denardo et al. |
| 2003/0147046 A1 | 8/2003 | Shadduck |
| 2003/0149470 A1 | 8/2003 | Alvarado et al. |
| 2003/0149480 A1 | 8/2003 | Shadduck |
| 2003/0191276 A1 | 10/2003 | Lendlein et al. |
| 2004/0014929 A1 | 1/2004 | Lendlein et al. |
| 2004/0021874 A1 | 2/2004 | Shimmick |
| 2004/0024143 A1 | 2/2004 | Lendlein et al. |
| 2004/0030062 A1 | 2/2004 | Mather et al. |
| 2004/0068262 A1 | 4/2004 | Lemos et al. |
| 2004/0098110 A1 | 5/2004 | Williams et al. |
| 2004/0110285 A1 | 6/2004 | Lendlein et al. |
| 2004/0117955 A1 | 6/2004 | Barvosa-Carter et al. |
| 2004/0122174 A1 | 6/2004 | Mather et al. |
| 2004/0138678 A1 | 7/2004 | Brown |
| 2004/0215192 A1 | 10/2004 | Justis, Jr. et al. |
| 2004/0243111 A1 | 12/2004 | Bendett et al. |
| 2004/0260298 A1 | 12/2004 | Kaiser et al. |
| 2005/0033163 A1 | 2/2005 | Duchon et al. |
| 2005/0033295 A1 | 2/2005 | Wisnewski |
| 2005/0070905 A1 | 3/2005 | Donnelly et al. |
| 2005/0090822 A1 | 4/2005 | Dipoto |
| 2005/0203622 A1 | 9/2005 | Steiner et al. |
| 2005/0212630 A1 | 9/2005 | Buckley et al. |
| 2005/0228500 A1 | 10/2005 | Kim et al. |
| 2005/0244353 A1 | 11/2005 | Lendlein et al. |
| 2006/0009785 A1 | 1/2006 | Maitland et al. |
| 2006/0030933 A1 | 2/2006 | Delegge et al. |
| 2006/0036045 A1 | 2/2006 | Wilson et al. |
| 2006/0041089 A1 | 2/2006 | Mather et al. |
| 2006/0095134 A1 | 5/2006 | Trieu et al. |
| 2006/0096044 A1 | 5/2006 | Miki et al. |
| 2006/0129232 A1 | 6/2006 | Dicarlo et al. |
| 2006/0136057 A1 | 6/2006 | Brulez et al. |
| 2006/0142794 A1 | 6/2006 | Lendlein et al. |
| 2006/0155287 A1 | 7/2006 | Montgomery et al. |
| 2006/0206140 A1 | 9/2006 | Shaolian et al. |
| 2006/0213522 A1 | 9/2006 | Menchaca et al. |
| 2006/0270749 A1 | 11/2006 | Salamone et al. |
| 2007/0004863 A1 | 1/2007 | Mentak |
| 2007/0078515 A1 | 4/2007 | Brady |
| 2007/0141339 A1 | 6/2007 | Song et al. |
| 2007/0298068 A1 | 12/2007 | Badawi et al. |
| 2007/0299487 A1 | 12/2007 | Shadduck |
| 2008/0004692 A1 | 1/2008 | Henson et al. |
| 2008/0021166 A1 | 1/2008 | Tong et al. |
| 2008/0141736 A1 | 6/2008 | Jones et al. |
| 2008/0177303 A1 | 7/2008 | Anthamatten et al. |
| 2008/0186551 A1 | 8/2008 | Hanft et al. |
| 2008/0228186 A1 | 9/2008 | Gall et al. |
| 2008/0236601 A1 | 10/2008 | Jacobus |
| 2008/0281405 A1 | 11/2008 | Williams et al. |
| 2009/0005777 A1 | 1/2009 | Houser et al. |
| 2009/0149617 A1 | 6/2009 | Gall et al. |
| 2009/0149952 A1 | 6/2009 | Shadduck |
| 2009/0222025 A1 | 9/2009 | Catanese, III et al. |
| 2009/0234449 A1 | 9/2009 | De, Jr. et al. |
| 2009/0248141 A1 | 10/2009 | Shandas et al. |
| 2010/0065975 A1 | 3/2010 | Chen |
| 2010/0119833 A1 | 5/2010 | Madsen et al. |
| 2010/0145445 A1 | 6/2010 | Aharoni et al. |
| 2011/0002464 A1 | 1/2011 | Lipshitz et al. |
| 2011/0144227 A1 | 6/2011 | Bowman et al. |
| 2011/0275675 A1 | 11/2011 | Rist et al. |
| 2012/0053313 A1* | 3/2012 | Higgs ............ A61L 27/16 526/286 |
| 2012/0232648 A1 | 9/2012 | Kahook et al. |
| 2014/0172094 A1 | 6/2014 | Kahook et al. |
| 2014/0277439 A1 | 9/2014 | Hu et al. |

FOREIGN PATENT DOCUMENTS

| | | |
|---|---|---|
| DE | 10207535 B4 | 7/2006 |
| EP | 0336318 A2 | 10/1989 |
| EP | 0368274 A2 | 5/1990 |
| EP | 0668055 A2 | 8/1995 |
| EP | 1231496 A2 | 8/2002 |
| EP | 1481640 A1 | 12/2004 |
| EP | 1607048 A1 | 12/2005 |
| EP | 1719483 A1 | 11/2006 |
| EP | 2683819 A2 | 1/2014 |
| JP | H02142778 A | 5/1990 |
| JP | 2003145564 A | 5/2003 |
| WO | 9213490 A1 | 8/1992 |
| WO | 9611721 A1 | 4/1996 |
| WO | 9838907 A1 | 9/1998 |
| WO | 2004014217 A2 | 2/2004 |
| WO | 2004110313 A1 | 12/2004 |
| WO | 2005011546 A1 | 2/2005 |
| WO | 2006108114 A2 | 10/2006 |
| WO | 2007001407 A2 | 1/2007 |
| WO | 2007038429 A1 | 4/2007 |
| WO | 2007089843 A2 | 8/2007 |
| WO | 2008051254 A1 | 5/2008 |
| WO | 2012040380 A1 | 3/2012 |
| WO | 2012122320 A2 | 9/2012 |
| WO | 2013040434 A1 | 3/2013 |
| WO | 2014085827 A1 | 6/2014 |
| WO | 2015038940 A1 | 3/2015 |

OTHER PUBLICATIONS

Author Unknown, "Brain Aneurysm Treatment," Boston Scientific Corporation, 2010, 2 pages.

Author Unknown, "Development of Aneurysm Treatment using Laser-Deployed Shape Memory Polymer Foams," University of California, Davis, 2002-2009, 3 pages.

Author Unknown, "Embolic Coils," International Neuro Products, 2010, 1 page.

Author Unknown, "Enhanced Embolic Coils for the Treatment of Cerebral Aneurysms," Micrus Endovascular, 2010, 3 pages.

Author Unknown, "ePAX," NeuroVasx, 1 page.

Author Unknown, "Shape Memory Therapeutics Receives Texas Emerging Technology Fund Award," Texas A&M University, 2009, 2 pages.

Author Unknown, "HydroCoil," MicroVention Terumo, 2010, 2 pages.

Author Unknown, "HydroSoft," MicroVention Terumo, 2010, 2 pages.

Author Unknown, "Matrix2 Detachable Coils," Boston Scientific Corporation, 8 pages.

Author Unknown, "MicroPlex Coil System," MicroVention Terumo, 2010, 1 page.

Author Unknown, "Neurovascular Intervention," Boston Scientific Corporation, 2010, 2 pages.

Author Unknown, "Trufill DCS Orbit Detachable Coil System," Codman & Shurtleff, Inc., 2000-2010, 2 pages.

Author Unknown, "VortX 18 and 35 Vascular Occlusion Coils," Boston Scientific Corporation, 2010, 2 pages.

Bellin I., et al., "Polymeric Triple-Shape Materials," Proceedings of the National Academy of Sciences, 2006, vol. 103 (48), pp. 18043-18047.

Cambridge Journals: MRS Table of Contents for vol. 855, 2004. MRS Online Processings Library, Online, Retrieved on [Jun. 26, 2014]. Retrieved from intent URL: http://journals.cambridge.org/action/displayIssue?id=OPL&volumeId=855&seriesId=0&issueId=-1.

De Nardo L., et al., "Shape Memory Polymer Foams for Cerebral Aneurysm Reparation: Effects of Plasma Sterilization on Physical Properties and Cytocompatibility," Acta Biomaterialia, 2009, vol. 5 (5), pp. 1508-1518.

Diani., et al., "Finite Strain 3D Thermoviscoelastic Constitutive Model for Shape Memory Polymers," Polymer Engineering & Science, 2006, vol. 46 (4), pp. 486-492.

(56) References Cited

OTHER PUBLICATIONS

El Feninat., et al., "Shape Memory Materials for Biomedical Applications," Advanced Engineering Materials, 2002, vol. 4 (3), pp. 91-104.

Franzesi., Design of a novel anterior cruciate ligament prosthesis, Massachusetts Institute of Technology Thesis, 2006, Retrieved from the Internet: URL: http://hdl.handle.net/1721.1/36693.

Gall., et al., "Shape Memory Polymer Nanocomposites," Acta Materialia, 2002, vol. 50 (20), pp. 5115-5126.

Gall., et al., "Shape-Memory Polymers for Microelectromechanical Systems," Journal of Microelectromechanical Systems, 2004, vol. 13 (3), pp. 472-483.

Gall., et al., "Thermomechanics of the Shape Memory Effect in Polymers for Biomedical Applications," Journal of Biomedical Materials Research, 2005, vol. 73 (3), pp. 339-348.

Hampikian J.M., et al., "Mechanical and Radiographic Properties of a Shape Memory Polymer Composite for Intracranial Aneurysm Coils," Materials, Science and Engineering, 2006, vol. 26 (8), pp. 1373-1379.

Heaton B.C., "A Shape Memory Polymer for Intracranial Aneurysm Coils: An Investigation of Mechanical and Radiographic Properties of a Tantalum-Filled Shape Memory Polymer Composite," Thesis Presented to Academic Faculty, Georgia Institute of Technology, Jul. 2004, 60 pages.

International Search Report and Written Opinion for Application No. PCT/US2006/15207, dated Aug. 18, 2006,4 pages.

International Search Report and Written Opinion for Application No. PCT/US2008/058249, dated Sep. 29, 2009, 15 pages.

International Search Report and Written Opinion for Application No. PCT/US2008/071066, dated Apr. 24, 2009, 11 pages.

International Search Report and Written Opinion for Application No. PCT/US2012/028150, dated Feb. 1, 2013, 10 pages.

International Search Report and Written Opinion for Application No. PCT/US2014/055459, dated Dec. 4, 2014, 12 pages.

International Search Report for Application No. PCT/US2007/065691, dated Sep. 21, 2007, 2 pages.

Jeon., et al., "Shape Memory and Nanostructure in Poly(Norbornyl-Poss) Copolymers," Polymer International, 2000, vol. 49 (5), pp. 453-457.

Langer., et al., "Designing Materials for Biology and Medicine," Nature, 2004, vol. 428 (6982), pp. 487-492.

Lendlein.A., et al., "Ab-Polymer Networks Based on Oligo(Epsilon-Caprolactone) Segments Showing Shape-Memory Properties," Proceedings of the National Academy of Sciences, 2001, vol. 98 (3), pp. 842-847.

Lendlein.A., et al., "Biodegradable, Elastic Shape-Memory Polymers for Potential Biomedical Applications," Science, 2002, vol. 296 (5573), pp. 1673-1676.

Lendlein.A., et al., "Shape-Memory Polymers As Stimuli-Sensitive Implant Materials," Clinical Hemorheology and Microcirculation, 2005, vol. 32 (2), pp. 105-116.

Lendlein.A., et al., "Light-Induced Shape-Memory Polymers," Nature, 2005, vol. 434 (7035), pp. 879-882.

Lin., et al., "Study on Shape-Memory Behavior of Polyether-Based Polyurethanes. I. Influence of the Hard-Segment Content," Journal of Applied Polymer Science, 1998, vol. 69 (8), pp. 1563-1574.

Lin., et al., "Study on Shape-Memory Behavior of Polyether-Based Polyurethanes. Ii. Influence of Soft-Segment Molecular Weight," Journal of Applied Polymer Science, 1998, vol. 69 (8), pp. 1575-1586.

Liu., et al., "Chemically Cross-Linked Polycyclooctene: Synthesis, Characterization, and Shape Memory Behavior," Macromolecules, 2002, vol. 35 (27), pp. 9868-9874.

Liu., et al., "Thermomechanical Recovery Couplings of Shape Memory Polymers in Flexure," Smart Materials and Structures, 2003, vol. 12 (6), pp. 947-954.

Liu., et al., "Thermomechanics of Shape Memory Polymers: Uniaxial Experiments and Constitutive Modeling," International Journal of Plasticity, 2006, vol. 22 (2), pp. 279-313.

Maitland D.J., et al., "Design and Realization of Biomedical Devices Based on Shape Memory Polymers," Materials Research Society, Online Proceedings Library, 2009, Retreived from the internet: URL: www.mrsorq.

Maitland D.J., et al., "Prototype Laser-activated Shape Memory Polymer Foam Device for Embolic Treatment of Aneurysms," Journal of Biomedical Optics, 2007, vol. 12 (3), 3 pages.

Maitland., et al., "Photothermal Properties of Shape Memory Polymer Micro-Actuators for Treating Stroke," Lasers in Surgery and Medicine, 2002, vol. 30 (1), pp. 1-11.

Metcalfe., et al., "Cold Hibernated Elastic Memory Foams for Endovascular Interventions," Biomaterials, 2003, vol. 24 (3), pp. 491-497.

Metzger., et al., "Mechanical Properties of Mechanical Actuator for Treating Ischemic Stroke," Biomedical Microdevices, 2002, vol. 4 (2), pp. 89-96.

Notice of Allowance dated Sep. 30, 2015 for U.S. Appl. No. 14/148,617, filed Jan. 6, 2014.

Rupp., et al., "Resulting Tensile Forces in the Human Bone-Patellar Tendon-Bone Graft: Direct Force Measurement in Vitro," Arthroscopy, 1999, vol. 15 (2), pp. 179-184.

Small W.IV., et al., "Biomedical Applications of Thermally Activated Shape Memory Polymers," Journal of Materials Chemistry, 2010, vol. 20 (18), pp. 3356-3366.

Van der Mooren et al., Effects of glistenings in intraocular lenses, Biomedical Optics Express, Aug. 1, 2013; 4(8): 1294-1304.

Polymer Properties Database, Glass Transition Temperatures, Apr. 4, 2018, http://polymerdatabase.com/polymer%20physics/Polymer%20Tg%20C.html.

Boppart S.A., et al., "High-Resolution Optical Coherence Tomography-Guided Laser Ablation of Surgical Tissue," Journal of Surgical Research, 1999, vol. 82 (2), pp. 275-284.

International Search Report and Written Opinion for Application No. PCT/US2007/06591, dated Dec. 8, 2007, 5 pages.

Loesel F.H., et al., "Non-thermal Ablation of Neural Tissue with Femtosecond Laser Pulses," Applied Physics B, Jan. 1998, vol. 66 (1), pp. 121-128.

Lubatschowski H., "Sight Scalpel—OCT-controlled microsurgery with ultrashort laser pulses," Laser Technik Journal, Nov. 2005, vol. 2 (4), pp. 63-66.

Smith.T, "Time and Temperature Dependence of the Ultimate Properties of an Sbr Rubber at Constant Elongations," Journal of Applied Physics, 1960, vol. 31 (11), pp. 1892-1898.

Smith.T, "Strength of Elastomers," Polymer Engineering and Science, 1977, vol. 17 (3), pp. 129-143.

Smith.T, "Ultimate Tensile Properties of Elastomers. I. Characterization by a Time and Temperature Independent Failure Envelope," Journal of Polymer Science, 1963, vol. 1 (12), pp. 3597-3615.

Sokolowski., et al., "Medical Applications of Shape Memory Polymers," Biomedical Materials, 2007, vol. 2, pp. S23-S27.

Sokolowski W.M., et al., "Cold Hibernated Elastic Memory (CHEM) Self-Deployable Structures," SPIE 99 International Symposium on Smart Structures and Materials, 1999, pp. 179-185.

Supplementary European Search Report for Application No. EP07759877, dated Feb. 14, 2011, 5 pages.

Supplementary European Search Report for Application No. EP12755496, dated May 21, 2015, 7 pages.

Takahashi., et al., "Structure and Properties of Shape-Memory Polyurethane Block Copolymers," Journal of Applied Polymer Science, 1996, vol. 60, pp. 1061-1069.

Tobushi., et al., "Thermomechanical Constitutive Modeling in Shape Memory Polymer of Polyurethane Series," Journal of Intelligent Material Systems, 1997, vol. 8 (8), pp. 711-718.

Tobushi., et al., "Theunomechanical Properties in a Thin Film of Shape Memory Polymer of Polyurethane Series," Smart Materials and Structures, 1996, vol. 5 (4), pp. 483-491.

Wache., et al., "Development of a Polymer Stent With Shape Memory Effect As a Drug Delivery System," Journal of Materials Science, 2003, vol. 14 (2), pp. 109-112.

Wilson T.S., et al., "Shape Memory Polymer Therapeutic Devices for Stroke," Smart Medical and Biomedical Sensor Technology III, 2005, 8 pages.

(56) References Cited

OTHER PUBLICATIONS

Yakacki C.M., et al., "Optimizing the Thermomechanics of Shape-Memory Polymers for Biomedical Applications," Materials Research Society Symposium Proceedings 2005, vol. 855E, pp. W3.27.1-W3.37.6.

Yakacki C.M., et al., "Thermomechanics of Shape-Memory Polymers for Biomedical Applications," Materials Research Society, University of Colorado, Boulder, 2004.

Yakacki C.M., et al., "Strong, Tailored, Biocompatible Shape-Memory Polymer Networks," Advanced Functional Materials, 2008, vol. 8 (16), pp. 2428-2435.

Zhu., et al., "Shape-Memory Effects of Radiation Crosslinked Poly(E-Caprolactone)," Journal of Applied Polymer Science, 2003, vol. 90 (6), pp. 1589-1595.

\* cited by examiner

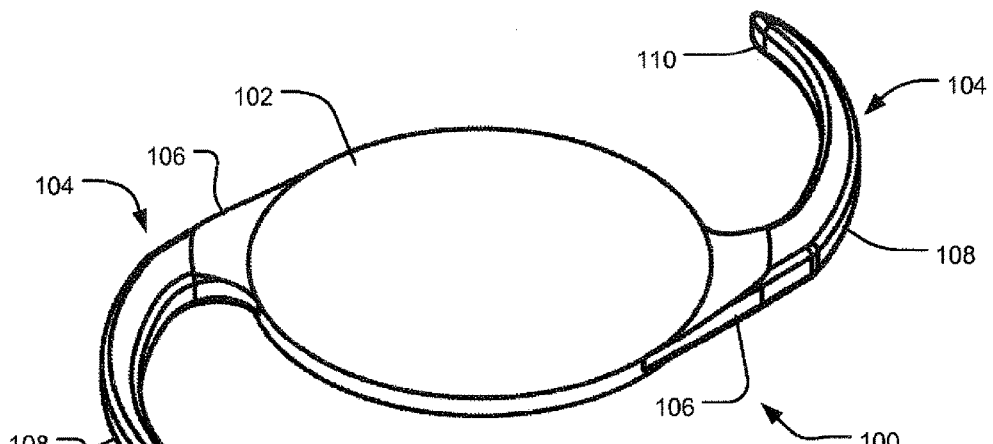
Fig. 8A
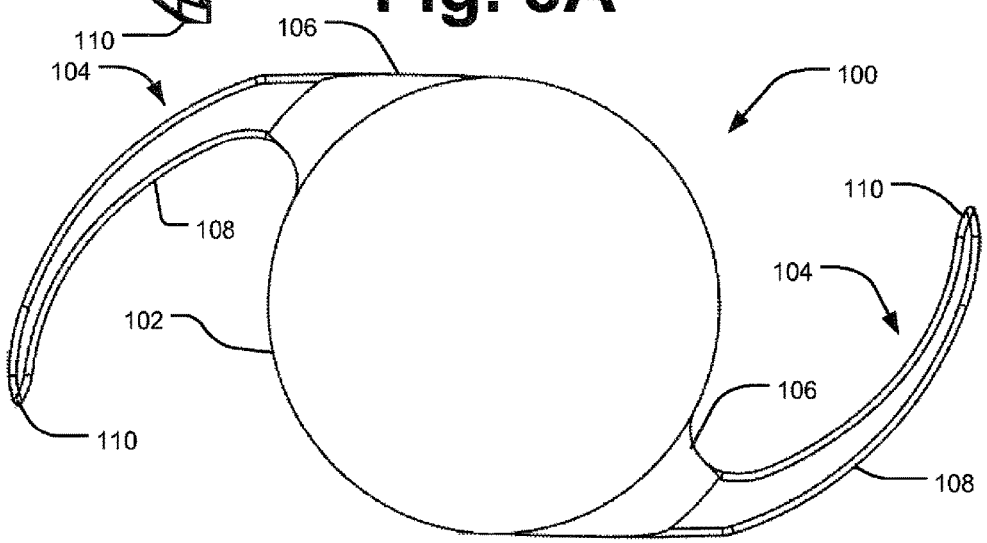
Fig. 8B
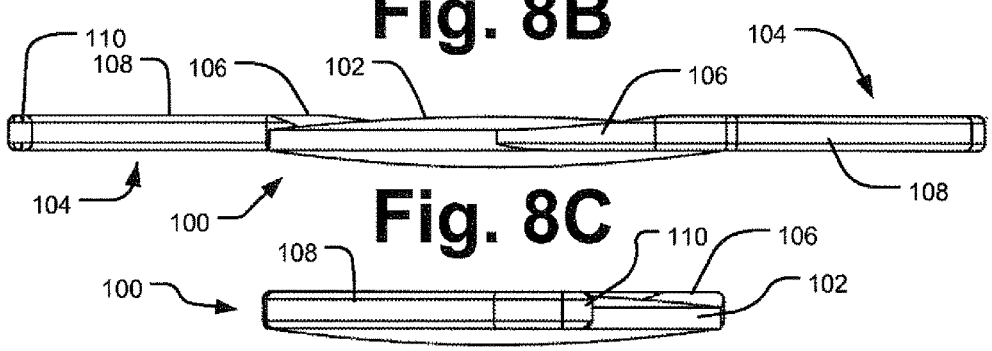
Fig. 8C
Fig. 8D

INTRAOCULAR LENSES

CROSS REFERENCE TO RELATED APPLICATIONS

This application is continuation of U.S. patent application Ser. No. 14/026,832, filed 19 Jun. 2014, now U.S. Pat. No. 9,427,493, which is a continuation-in-part of U.S. patent application Ser. No. 13/441,754, filed on 6 Apr. 2012, now U.S. Pat. No. 8,685,089, which is a continuation of U.S. patent application Ser. No. 13/500,884, filed 6 Apr. 2012, now abandoned, which is a national stage entry under 35 U.S.C. 371 of International Patent Application No. PCT/US2012/028150, filed on 7 Mar. 2012, which claims the benefit of priority pursuant to 35 U.S.C. 119(e) of U.S. provisional application No. 61/449,865 filed 7 Mar. 2011 entitled "Shape memory polymer intraocular lenses" and U.S. provisional application No. 61/474,696 filed 12 Apr. 2011 entitled "Shape memory polymer intraocular lenses," all of which are hereby incorporated herein by reference in their entirety.

TECHNICAL FIELD

The technology described herein relates to artificial intraocular lenses.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Intraocular lenses are employed as replacements for the crystalline lens after either extracapsular or intracapsular surgery for the removal of a cataract. In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

Intraocular lenses are generally of two types, those that are placed in the anterior chamber, i.e., between the iris and the cornea, and those that are placed in the posterior chamber, i.e., behind the iris. Both types of lenses are conventionally employed with the choice between an anterior chamber and a posterior chamber lens being partly dictated by requirements of the patient and partly dictated by the preferences of the physician inserting the lens. A third type of lens, known as iris-fixated lenses because they are secured to the iris periphery, can be thought of as being within one of the two types above, in that their optic portion is in either the anterior or posterior chamber.

Intraocular lenses normally consist of an optic with at least one and preferably two or more haptics that extend generally radially from the optic and contain distal portions that normally seat in the scleral spur for an anterior chamber lens and either in the ciliary sulcus or within the lens capsule for a posterior chamber lens. The optic normally comprises a circular transparent optical lens. The haptic in most lenses is a flexible fiber or filament having a proximate end affixed to the lens and having a distal end extending radially away from the periphery of the lens to form a seating foot. Several haptic designs are currently in use, for example, a pair of C-shaped loops in which both ends of each loop are connected to the lens, and, for example, J-shaped loops in which only one end of the loop is affixed to the lens.

Haptics are usually radially resilient and extend outwardly from the periphery of the lens and gently, but elastically, engage appropriate circumferential eye structures adjacent the iris or within the capsular bag. This resiliency is due to the conventional elastic properties of the materials of the haptic. The result is a haptic which when compressed and released will uncontrollably spring back immediately. This property makes the process of implantation and final positioning of the lens difficult since the haptics must be constrained during implantation. Also, once situated, the flexibility of the conventional haptic material makes the lens susceptible to decentration from being pushed by vitreous pressure from behind the lens or shifting due to pressure from adjacent ocular tissue. Also, the forces generated by the elastic recoil of the haptic release may damage the delicate local tissue.

The optimum position for a posterior chamber lens is in the capsular bag. This is an extremely difficult maneuver for the surgeon to accomplish. When a posterior chamber lens is employed it must be placed through the small pupillary opening, and the final haptic position is hidden behind the iris and not visible to the surgeon. It is therefore highly desirable to keep the overall dimensions of the posterior chamber lens as small as possible during implantation, letting it expand when it is finally situated where the surgeon intends, usually in the capsular bag. A small device is easier to manipulate in the eye, reduces the chance of the haptics coming in contact with the corneal endothelial tissue, and allows the surgeon ease of insertion, as he must often insert a lens with a 14 mm overall dimension through a pupil of 5 to 8 mm diameter. A smaller lens also reduces the lens/iris contact and can better guarantee that the intraocular lens and its haptics will be in the capsular bag.

In recent years intraocular lenses with and without haptics having relatively soft body portions have been provided such that the body portion could be folded generally across the diameter thereof for insertion into a smaller opening during implantation of the lens. Lenses formed of liquid or hydrogel constrained within a sheath have been designed which allow the lens body to be folded before insertion and then subsequently filled when in position. Unfortunately, the soft materials used for the bodies of these lenses lack the restorative strength sometimes required to return to their original shape.

Further, these lens types are typically deployed using either an elastic release mechanism, wherein mechanical energy stored by bending the elastic material is released when the mechanical constraint is removed, or through water uptake, also known as hydration, wherein the lens gradually absorbs water through an osmotic diffusion process. Both processes are difficult to control. In the former case, the elastic recoil may damage local tissue or may move the lens away from the center. In the latter case, the ultimate shape of the lens may become distorted if the expanding lens comes into contact with surrounding tissue. Further, hydrating materials are known to possess poor shape recovery properties.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can be focused alternatively on near and far objects. As the lens ages, it also becomes harder and is less able to change shape in reaction to the tightening of the ciliary muscle. This makes it harder for the lens to focus on near objects—a medical condition known as presbyopia. Presbyopia affects nearly all adults over the age of 45 or 50.

Typically, when a cataract or other disease requires the removal of the natural lens and replacement with an artificial IOL, the IOL is a monofocal lens, requiring that the patient use a pair of spectacles or contact lenses for near vision. Some bifocal IOLs have been created, but are not been widely accepted. Some IOL designs are single optic lenses having flexible haptics that allow the optic to move forward and backward in reaction to movement of the ciliary muscle. However, the amount of movement of the optic in these single-lens systems may be insufficient to allow for a useful range of accommodation. In addition, the eye must be medicated for one to two weeks to decrease eye movement in order for capsular fibrosis to entrap the lens that thereby provide for a rigid association between the lens and the capsular bag. Further, the commercial models of these lenses are made from a hydrogel or silicone material. Such materials are not resistive to the formation of posterior capsule opacification ("PCO"). The treatment for PCO is a capsulotomy using a Nd:YAG laser that vaporizes a portion of the posterior capsule. Such destruction of the posterior capsule may destroy the mechanism of accommodation of these lenses.

Known accommodative lenses also lack extended depth of focus in addition to having poor accommodation performance. Such known lenses further require precise lens sizing for proper function over a range of capsular bag sizes and lack long-term capsular fixation and stability. Further, as current lens replacement surgeries move towards smaller incision size, IOLs in general require the ability to be delivered through such small incisions.

Dual-optic lenses leverage the ability of the ciliary body-zonule complex to change the shape of the capsular bag. This allows the inter-lens distance to change, thereby allowing a change in refractive error. These dual-optic lenses can be large secondary to the optical hardware needed to create this optical system and requires larger corneal incisions to insert into the eye.

Intracorneal lenses are designed to treat refractive error or presbyopia. Intracorneal lenses include corneal implants and lenses, which are inserted through a small incision in the cornea created by a blade or a laser. The pocket formed by the incision in the cornea is used to position the implant to change the shape of the cornea. In the case of a lens implant, the pocket is used to position the refractive lens in the optically effective location. Some lenses create a pinhole-type effect to treat presbyopia. As current intracorneal lenses move towards smaller incision size, devices in general require the ability to be delivered through such small incisions. Laser technology such as the femtosecond laser has enhanced the ability to create these smaller corneal wounds and pockets for implantation.

Phakic intraocular lenses are implanted either in the anterior chamber supported by the angle structures or in the posterior sulcus immediately posterior to the iris and anterior to the native lens. The lens is implanted through a minimally invasive wound at the limbus and inserted into or through the anterior chamber. The lenses are used to treat refractive error and have the risk of causing trauma to the lens and/or angle structures. Smaller incisions require folding the lens and then lens deployment in the eye, which increases the risk of damage to intraocular structures.

Known acrylic lens materials are unable to be compressed significantly to achieve desired functionality for IOLs. While various methodologies are known to fold or roll acrylic IOLs, these merely address the need to reduce the form factor of a deployed shape for the purposes of minimizing the required incision size for implantation. The actual volume displaced by these lenses remains constant so there is a limit on the minimum size that such IOLs can reach. Further, the ability to fold or roll these IOLs is limited by the ability of the material to resist strain caused by the stress of folding and return to a desired shape and provide the necessary optical qualities after implantation. Further, there is little control over the speed and force with which deployment of a lens occurs once it is implanted, which often causes trauma to tissues which engage haptics of the IOL.

The information included in this Background section of the specification, including any references cited herein and any description or discussion thereof, is included for technical reference purposes only and is not to be regarded subject matter by which the scope of the invention as defined in the claims is to be bound.

SUMMARY

Shape-memory polymers (SMP) are a class of smart materials that can be tailored to have significant mechanical property changes in response to a given stimulus. The ability to recover from large deformations and adapt to differing environmental conditions greatly facilitates use of SMP devices in minimally invasive surgery. Current shape memory polymer formulations can be created to have independently programmed modulus and glass transition temperatures (Tg). The ability to precisely control mechanical properties of SMP along with the transparent nature of the material, a refractive index in ranges very similar to the range of a human lens (1.386-1.406 and greater), and proven biocompatibility allows for the creation of unique solutions for treatment of various ophthalmic diseases. Therefore, there are many aspects of a hydrophobic, acrylate-based, SMP intraocular lens which are appealing in view of other lens options.

One clear advantage of the SMP systems disclosed herein is the dramatic capability to vary mechanical properties by changing material properties such as cross-linked weight percentage, fractions of each component co-monomer, and other ingredient properties. This provides the capability to design the required mechanical properties for the specific application into the material. For example, varying Tg for particular SNIP formulations affects resultant rubbery modulus. Additional property changes can be incorporated, for example, by varying the weight percentage of the co-monomers forming the SMP. The SMP material qualities may also be leveraged to change the radius of curvature of the anterior and posterior surfaces of particular IOL designs with heat, UV light, or other processes to change the central and for paracentral power of the particular lens.

A variety of intraocular lenses may be formed of a shape memory polymer with high degrees of "shape certainty" or "shape-fixity" (i.e., the accuracy of the recovered shape after transition from the deformed shape back to the permanent shape). The lenses are deformed and compressed into a compact preoperative shape that allows for implantation through a small incision, gently unfurl and expand into guaranteed post-operative shapes (permanent shapes), and provide an integrated haptic for a stable and nontraumatic apposition to ciliary sulcus, capsular bag, or anterior chamber angle structures. The SMP lenses may be deformed and compressed to sizes smaller than currently known and available for implantation through an incision size under 2 mm, which is currently the lower limit.

In one exemplary implementation, a method of manufacturing an intraocular device includes providing a shape memory polymer (SMP) material with a Tg, forming the SMP material in a permanent intraocular device form, mechanically compressing the intraocular device at a temperature above Tg to deform the intraocular device into a smaller volume; and cooling the deformed intraocular device while still in compression to a temperature below Tg to thereby create a stable deformed intraocular device with a delivery profile allowing for insertion through an incision of 2 mm or less. In one embodiment, the intraocular device may be rolled at a temperature above Tg of the SMP material. The rolled intraocular device may then be cooled while still in a rolled form to a temperature below Tg to thereby create a stable rolled intraocular device. The intraocular device may then be mechanically compressed to a diameter of less than 1.8 mm. In another embodiment, the intraocular device may be rolled at a temperature above Tg of the SMP material. The intraocular device may then be radially compressed within a die to a diameter of less than 1.8 mm while maintaining the temperature above Tg.

In another exemplary implementation, a shape memory polymer (SMP) intraocular lens may have a refractive index above 1.45, a Tg between 15° C. and 40° C., inclusive, de minimis or an absence of glistening, and substantially 100% transmissivity of light in the visible spectrum. In one embodiment, the SMP intraocular lens may be formed of a combination of 50 weight percent tBA, 28 weight percent isobutyl acrylate, and 22 weight percent PEGDMA 1000. In another embodiment, the SMP intraocular lens may be formed of a combination of 22 weight percent tBA and 78 weight percent PEGDMA 1000. In a further embodiment, the SMP intraocular lens may be formed of a combination of 65 weight percent tBA, 13 weight percent butyl acrylate, and 22 weight percent PEGDMA 1000.

In another exemplary implementation, a shape memory polymer (SMP), such as in an IOL, may be derived from a formulation comprising: tertbutyl acrylate (tBA); one or more poly(ethylene glycol) dimethacrylate (PEGDMA) monomers; optionally one or more UV-blockers; optionally one or more polymerization initiators; optionally n-butyl acrylate (nBA); and optionally 2-hydroxy-3-phenoxypropyl acrylate (HPPA). The SMP may be derived from a formulation comprising 50-85 wt % tBA. The SMP may be derived from a formulation comprising 0.25-25 wt % PEGDMA, 0.5-25 wt % PEGDMA, or 3-25 wt % PEGDMA. The SMP may be derived from a formulation comprising 0-1.5 wt % UV-blockers, or 0.25-1.5 wt % UV-blockers. The SMP may be derived from a formulation comprising 0-3.0 wt % polymerization initiators, or 0.05-3.0 wt % polymerization initiators. The SMP may be derived from a formulation comprising 0-20 wt % nBA. The SMP may be derived from a formulation comprising 0-20 wt % HPPA. The SMP may be derived from a formulation comprising 50-85 wt % tBA; 3-25 wt % PEGDMA; 0.25-1.5 wt % UV-blockers; 0.05-3.0 wt % polymerization initiators; 0-20 wt % nBA; and 0-20 wt % HPPA.

The PEGDMA may be selected from the group consisting of: PEGDMA 550; PEGDMA 750; PEGDMA 1000; and PEGDMA 2000; or any combination thereof. The PEGDMA may be PEGDMA 750. The PEGDMA may be PEGDMA 1000.

The one or more UV-blockers may be selected from the group consisting of: a methacryloyl chlorobenzotriazole; a methacryloyl methoxybenzotriazole; and a yellow dye; or any combination thereof. The UV-blocker may be selected from the group consisting of: 2-methylacrylic acid 3-[3-tert-butyl-5-(5-chlorobenzotriazol-2-yl)-4-hydroxyphenyl]-propyl ester (UVB); and 2-(2-hydroxy-3-tert-butyl-5-vinylphenyl)-5-chloro-2H-benzotriazole (UVAM). The UV-blocker may be 3-(tert-butyl)-4-hydroxy-5-(5-methoxy-2H-benzo[d][1,2,3]triazol-2-yl)phenethyl methacrylate.

The one or more polymerization initiators may be selected from the group consisting of: 2,2-dimethoxy-2-phenylacetophenone (Irgacure 651); phenylbis(2,4,6-trimethylbenzoyl) phosphine oxide (Irgacure 819); azobisisobutyronitrile (AIBN); lauroyl peroxide; di(4-tert-butylcyclohexyl) peroxydicarbonate (Perkadox 16); camphorquinone; and diphenyl-(2,4,6-trimethylbenzoyl)-phosphine oxide (TPO); or any combination thereof. The polymerization initiator may be lauroyl peroxide. The polymerization initiator may include a photo initiator and a thermal initiator.

The shape memory polymer material may be derived from a formulation selected from the group consisting of SMP 208, SMP209, SMP210, SMP211, SMP213, SMP214, SMP215, SMP218, SMP219, and SMP230b, wherein SMP208 comprises tBA. (77.5%), UVB (0.5%), PEGDMA1000 (22%), and IRGACURE819 (0.15%); SMP209 comprises tBA (77.0%), UVB (1.0%), PEGDMA1000 (22%), and IRGACURE819 (0.15%); SMP210 comprises tBA (76.0%), UVB (2.0%), PEGDMA1000 (22%), and IRGACURE819 (0.15%); SMP211 comprises tBA (77.5%), UVAM (0.5%), PEGDMA1000 (22%), and IRGACURE819 (0.15%); SMP212 comprises tBA (77.0%), UVAM (1.0%), PEGDMA1000 (22%), and IRGACURE819 (0.15%); SMP213 comprises tBA (76.0%), UVAM (2.0%), PEGDMA1000 (22%), and IRGACURE819 (0.15%); SMP214 comprises tBA (77.3%), UVB (0.7%), PEGDMA1000 (22%), and IRGACURE819 (0.15%); SMP215 comprises tBA (77.45%), UVAM (0.55%), PEGDMA1000 (22%), and IRGACURE819 (0.15%); SMP218 comprises tBA (64.30%), nBA (13.0%), UVB (0.7%), PEGDMA1000 (22%), and IRGACURE819 (0.15%); SMP219 comprises tBA (64.45%), nBA (13.0%), UVAM (0.55%), PEGDMA1000 (22%), and IRGACURE819 (0.15%); and SMP230b comprises tBA (59.80%), nBA (12.00%), UVB (0.80%), PEGDMA1000 (10%), lauroyl peroxide (0.15%), and HPPA (17.50%); wherein UVB is 2-methylacrylic acid 3-[3-tert-butyl-5-(5-chlorobenzotriazol-2-yl)-4-hydroxyphenyl]-propyl ester; UVAM is 2-(2-hydroxy-3-tert-butyl-5-vinylphenyl)-5-chloro-2H-benzotriazole (UVAM); and IRGACURE819 is phenylbis(2,4,6-trimethylbenzoyl) phosphine oxide. The shape memory polymer material may be derived from a formulation comprising: 59.80 wt % tBA; 12.00 wt % nBA; 17.50 wt % HPPA; 0.70 wt % 2-methylacrylic acid 3-[3-tert-butyl-5-(5- chlorobenzotriazol-2-yl)-4-hydroxyphenyl]-propyl ester (UVB); 10 wt % PEGDMA 1000; and 0.15 wt % lauroyl peroxide.

An intraocular lens comprising the shape memory polymer material may have a refractive index above 1.45; a Tg between 10° C. and 60° C., inclusive; de minimis or an absence of glistening; and substantially 100% transmissivity of light in the visible spectrum.

In another exemplary implementation, a shape memory polymer (SMP), such as in an IOL, may be derived from a formulation comprising: tertbutyl acrylate (tBA); one or more polyethylene glycol) dimethacrylate (PEGDMA) monomers; optionally n-butyl acrylate (nBA); and optionally 2-hydroxy-3-phenoxypropyl acrylate (HPPA).

In a further exemplary implementation, a method of implanting an intraocular lens device includes making an incision in a cornea or sclera less than 2 mm wide. In one embodiment, an intraocular lens is inserted into the capsular bag through the incision. In another embodiment, an intraocular lens is inserted into the ciliary sulcus through the incision. In another embodiment, a method of implanting an intraocular lens device includes making an incision into a cornea less than 2 mm wide to access the anterior chamber. An intraocular lens is then inserted into the anterior chamber through the incision. In a further embodiment, a method of implanting an intracorneal implant device includes making an incision into a cornea less than 2 mm wide to create a tunnel in the cornea. An intracorneal implant device is then inserted into the anterior chamber through the incision.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 8A is an isometric view of an exemplary shape memory polymer (SMP) intraocular lens (IOL) with placement haptics in a permanent or deployed configuration.

FIG. 8B is a top plan view of the SMP IOL of FIG. 1A.

FIG. 8C is a front elevation view of the SMP IOL of FIG. 1A.

FIG. 8D is a side elevation view of the SMP IOL of FIG. 1A.

DETAILED DESCRIPTION

Figure 1:
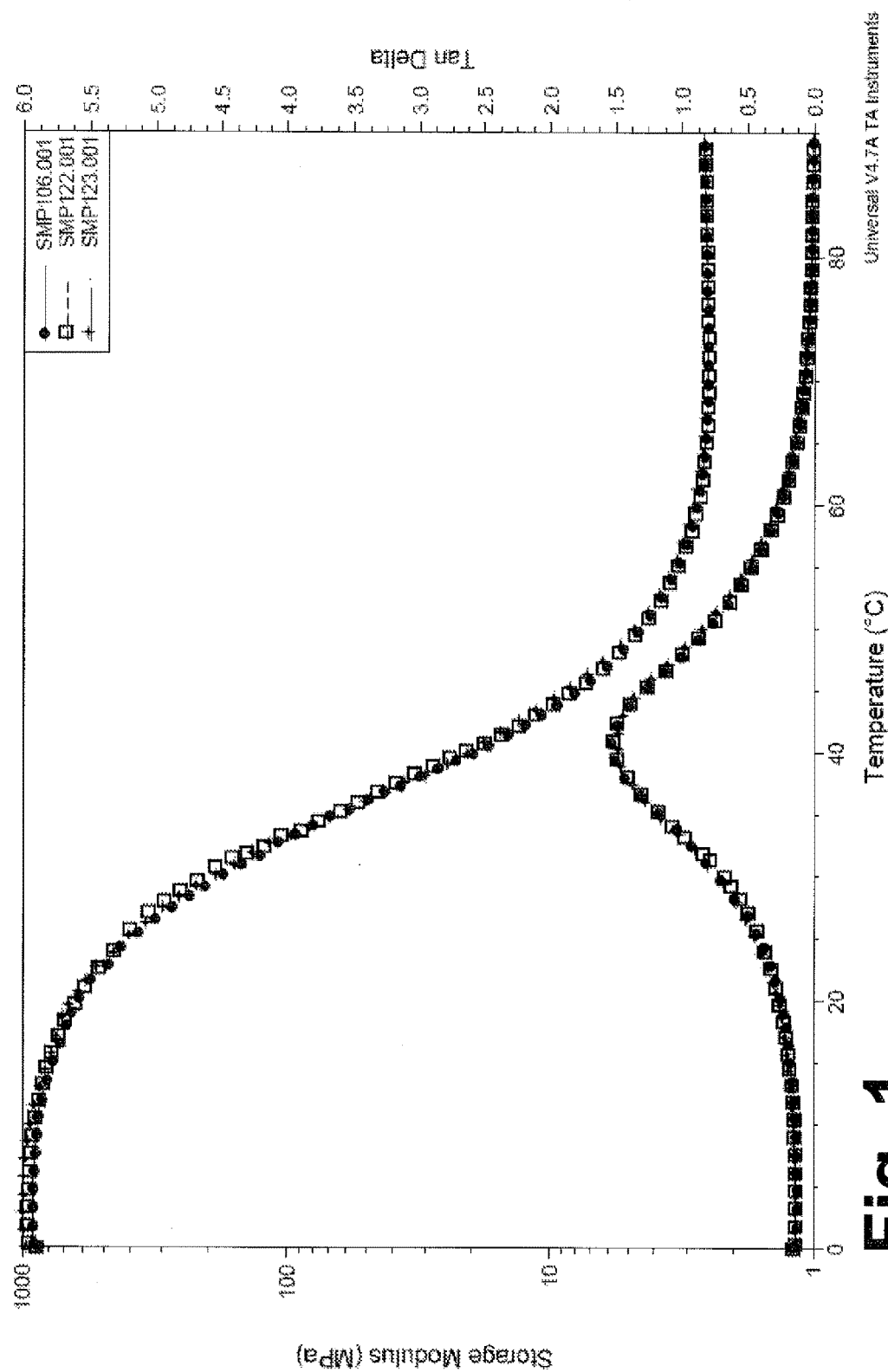
FIG. 1 is a graph depicting the storage modulus vs. temperature attributes for several exemplary SMP formulations.

The SMP IOLs disclosed herein are more deformable than known acrylic lens materials (in some cases greater than 65% compression and greater than 250% tensile strain) and thus the volume displaced by such devices can actually be reduced for implantation. This allows for implantation through reduced incision sizes (sub 2 mm and even sub 1.8 mm) and thus reduced trauma to the human eye. Several other benefits are also achievable by using SMP IOLs disclosed herein.

The refractive index of many of the formulations ($n_0 \approx 1.464$) is relatively high (higher than the refractive index of human lens tissue) and thus allows for the possibility of reducing the thickness of the lens and therefore of the size of the delivery profile. The refractive index of SMP IOLs can further be modified by formulation of the SMP material.

The formulations of the SMP materials can be adjusted to slow or time delay the shape recovery process in order to reduce trauma to tissue in the implant location and to allow the surgeon adequate time for manipulation and placement of the IOL in the proper location. With some SMP formulations, post implant modification is possible, e.g., to change the curvature of the optic or the index of refraction. This may be realized through application of non-intrusive heating of the SMP IOL, or portions thereof, post-implant via laser or ultrasound. Such heating may be applied to particular sections of the SMP IOL which have different cross-link weight percentages of material (and thus different Tg in those areas) to allow activation of a secondary or tertiary shape change, which may be used to effect changes to the refractive index, the curvature of the optic, or the expansion of the haptics. For example, the configuration of the haptic-optic junction may be changed to modify the vault of the optic by heating the junction. Such secondary or tertiary shape changes may also be used to promote interaction with the lens capsule, vitreous, zonules and surrounding tissues to help in accommodation. In addition, the baseline positioning of the two optics in a dual optic accommodative intraocular lens system can be changed even after implantation.

The SMP materials may provide extremely high shape fixity (>95-99%). The higher the shape fixity, defined as the percent change in recovered shape compared to the original molded shape, the higher the reproducibility and confidence that the deployed IOL will function as intended (e.g., the post deployment shape of IOLs should be highly controlled to maximize the optical characteristics of the device). The SMP materials disclosed herein provide extremely high shape fixity in large part because the SMP materials deploy using a non-elastic, non-melt shape recovery process (i.e., it is not a phase change using fluid properties). Further, the SMP materials are not a hydrogel or other type of hydrating material. The SMP materials transform from one highly-reproducible, non-changing, non-creeping, non-deforming, storage shape, to another highly-reproducible, non-changing, non-creeping, non-deforming, secondary (permanent) shape.

The SMP materials may have a pre-programmed shape; and post-deployment the SMP devices release internal stored energy to move to the programmed shape, which may or may not be adaptive to the local tissue. The local tissue does not play a part in shaping the form of the SMP devices. The SMP devices return to their "permanent" shape as originally formed when molded, before being deformed for smaller profile delivery. The speed of full deployment from the deformed state to the glass (permanent) state can be varied over a wide range from less than a second to over 600 seconds depending upon the SMP formulation.

The disclosed high Tg (i.e., at or above body temperature) SMP formulations provide for processes of packaging, shipping, storing, and ultimately implanting SMP devices that do not require refrigerated storage or ice or an otherwise low-temperature operating environment. Thus, a significant advantage of the SMP materials described herein is that they can be stored in the stored shape for extended periods of time, they can be packaged in constrained forms within a customized delivery system, and they can be deployed without need for prior refrigeration or other temperature changes. For example, during shipping of a device, the environmental effect of cycling of temperatures and inadvertent deployment of a device can be eliminated by constraining the device in a delivery system or packaging system.

Optionally, SMP IOL formulations disclosed herein may include (e.g., be impregnated with) various drugs that may be eluted from the SMP IOL once implanted in vivo to assist with the healing process of the optical tissue traumatized during implantation or to deliver therapeutic medications to treat other ocular diseases. The medication or active ingredient (e.g., a biologic agent) may be integrated into the SMP IOL as part of the polymerization process, within a swelling agent (e.g., as a chemical or physical hydrogel polymer structure), or as a biodegradeable, drug-eluting polymer portion of the final SMP IOL device. Exemplary drugs that may be impregnated in the SMP IOL may include antibiotics, anti-inflammatories, anti-histamines, anti-allergy, biologic agents (e.g., anti-VEGF agents, siRNAs, etc), and glaucoma medications (i.e., medications to decrease eye pressure, which include, but are not limited to, prostaglandins, parasympathetic/sympathetic-based medications, alpha agonists, beta blockers, carbonic anhydrase inhibitors, Rho Kinase inhibitors, adenosine agonists, endothelin agonists and antagonists, etc). Other agents that may be linked to an SMP IOL include viral vectors and cell-based therapeutics.

A variety of intraocular lens types can be made of SMP materials according to the formulations described below, having selected material properties to meet the needs of the particular lens type or design. Several of these lens options are also described below.

Shape Memory Polymer Materials

The SMP formulations disclosed herein allow IOLs to be created to meet specific design requirements. Further, the SMP formulations allow IOLs to be manufactured using scalable liquid injection manufacturing techniques. The SMP formulations disclosed herein can provide IOLs with the following advantageous properties: shape fixity of >98.5%; recovery rates of between 0.25 seconds to 600 seconds, including clinically desirable rates of between 3 and 25 seconds, inclusive; minimum device deformations of at least 40% in any dimension during the manufacturing process, and preferentially of 100-200%; rubbery modulus of 250 kPa to 20,000 kPa; tailoring of Tg for folding, compression, and injection; glistening-free (an industry term describing optical imperfections possible in polymer formulations for intraocular lenses); UV blocking capabilities; coloration of blue, yellow, red, and green, or combinations thereof; cycle times for liquid injection manufacturing of 30 seconds to 20 minutes; ability to tolerate high temperature mold-based manufacturing, e.g., temperatures of as much as 400 degrees; capability to tolerate high-pressure mold-based manufacturing, specifically pressures of as much as 50 Mpa; ability to flow through extremely narrow channels (<100 microns diameter) during the mold-based manufacturing process (i.e., low viscosity at manufacturing temperatures); and volume shrinkage to permanent shape of 3%-15% or less after thermal curing in the mold-based manufacturing process.

SMP materials have significant capacity to change shape or otherwise activate with a mechanical force in response to an external stimulus. The stimulus may be light, heat, chemical, or other types of energy or stimuli. The thermo-mechanical response of SMP materials may be controlled through formulation to predict and optimize shape-memory properties. Shape memory polymer devices may be designed and optimized to a high degree of tailorability that are capable of adapting and responding to particular biomedical applications and patient physiology.

A polymer may be considered a SMP if the original shape of the polymer can be deformed and remain stable in the deformed state until acted upon by an external stimulus, and then the original shape can be recovered by exposing the material to the appropriate stimulus. In one implementation, the stimulus may be heat. The original shape may be set by molding, extruding, stamping, or other typical polymer processing processes. In addition, a disc, rod, or other configuration of the material may be formed by the above processes and then shaped into a final shape with cryolathing, which is a process involving freezing of the material followed by laser and/or mechanical cutting of the material into a final shape. The temporary shape may be set by thermo-mechanical deformation. Heating the deformed SMP material above a shape deformation recovery temperature results in recovery of the original shape, even if the original molded shape of the polymer is altered mechanically at a lower temperature than the deformation recovery temperature. SMP materials disclosed for use in the applications herein have the ability to recover large deformation upon heating and in appropriate formulations with greater than 99% accuracy of the original shape.

In one implementation using heat stimulus, a polymer transition temperature may be tailored to provide for a deformation recovery temperature, at body temperature, about 37° C.; i.e., the glass transition temperature, Tg, of the polymer is designed to be about 37° C. The distinct advantage of this approach is the utilization of the thermal energy of the human body to naturally activate the SMP material. For some applications, the mechanical properties (e.g., stiffness) of the material are strongly dependent on Tg. Thus, it may be difficult to design an extremely stiff device when Tg is close to the body temperature due to the compliant nature of the polymer. Another consideration in medical applications is that the required storage temperature of a shape memory polymer with Tg about 37° C. will typically be below room temperature requiring "cold" storage before deployment. In higher temperature transportation or storage environments, the folded shape may be retained through the use of a constraining device which does not allow the device to deploy into its initially molded shape.

In an alternative implementation, the recovery temperature is higher than the body temperature, i.e., Tg>37° C. The advantage of this implementation is that the storage temperature can be equal to room temperature facilitating easy storage of the device and avoiding unwanted deployments before use. The folded shape may be retained through the use of a constraining device which does not allow the device to deploy into its initially molded shape. However, local heating of the material upon deployment may be needed to induce recovery of the SMP material. Local damage to some tissues in the human body may occur at temperatures approximately 5 degrees above the body temperature through a variety of mechanisms including apoptosis and protein denaturing. Local heating bursts may be used to minimize exposure to elevated temperatures and circumvent tissue damage. The use of one method over the other is a design decision that depends on the targeted body system and other device design constraints such as required in-vivo mechanical properties.

In order to deliver the IOLs through the smallest possible incision, the mechanical properties of the SMP devices may be developed to achieve high levels of recoverable strain. In tension, up to 180% strain can be achieved for 10% cross-linked systems and up to 60% strain can be achieved in 40% cross-linked systems. In compression 80% or more strain can be achieved with the above percentage cross-link. The desired levels of strain in tension and compression are determined by the level of deformation required to fit the SMP IOL into the delivery system. Formulations with lower amounts of cross-linking can undergo higher levels of deformation without failure. Current IOLs utilize 5%-40% cross-linking to achieve the material properties for the desired level of recoverable strain.

The SMP IOLs and SMP materials may have a refractive index of 1.45 or greater, 1.46 or greater, 1.47 or greater, 1.48 or greater, 1.49 or greater, or 1.50 or greater. The SMP IOL's and SMP materials may have a refractive index of at least 1.45, at least 1.46, at least 1.47, at least 1.48, at least 1.49, or at least 1.50.

The SMP IOL's and SMP materials may have an equilibrium water content of 8% or less, 7% or less, 6% or less, 5% or less, 4% or less, 3% or less, 2% or less, 1% or less, or 0.5% or less. The SMPs may have an equilibrium water content (EWC) of 0.5-3.0%. EWC may be gravimetrically determined by comparison of dry and hydrated sample weight. For example, first, the dry sample weight is obtained, then the sample is placed in a suitable container and equilibrated in de-ionized $H_2O$ at a prescribed temperature and time period (e.g., at least 24 h). The sample may then be removed from the de-ionized $H_2O$, excess surface water removed and the sample weighed. EWC may be determined by the following formula: % EWC=[($wt_{hyd}$−$wt_{dry}$)/$wt_{hyd}$]×100.

The SMP IOLs and SMP materials disclosed herein may exhibit little or no glistening. The term "glistenings," may refer to small, light reflective regions in an IOL structure. It is believed that glistenings may be caused by water entry into vacuoles in a polymeric matrix of an IOL, changing the refractive index of the lens at those points, which change appears as reflective spots or "glistenings." Glistenings can cause glare and other annoyances to patients who have implanted IOLs. Glistening may be measured by placing a sample (e.g., a coupon, lens, disk) in distilled water maintained at a selected temperature (e.g., 50° C.) for a selected time period (e.g., 72 hours). The sample may thereafter be removed from the DI water and inspected under a stereo microscope and/or by slit lamp microscopy. Magnifications of 10-80× may be used. The entire sample may be analyzed on both sides as well as at various angles to ensure complete inspection of the sample. A sample may be judged to have no glistenings if the number of glistenings detected in the eyepiece is zero.

Monomers for Manufacture of SMP Materials

SMP materials may be prepared from one or more monomers. The SMP components and amounts thereof may be selected in order to attenuate and/or select for various properties, such as shape memory, glass transition temperature, UV-blocking, refractive index, equilibrium water content (EWC), and glistening.

In certain embodiments, the SMP polymer segments can be natural or synthetic, although synthetic polymers are preferred. The polymer segments may be nonbiodegradable. Non-biodegradable polymers used for medical applications preferably do not include aromatic groups, other than those present in naturally occurring amino acids. The SMP utilized in the IOLs disclosed herein may be nonbiodegradable. In some implementations, it may be desirable to use biodegradable polymers in the SMP IOLs, for example, when temporary sterilization is desired or additional functionality is necessary.

The polymers may be selected based on the desired glass transition temperature(s) (if at least one segment is amorphous) or the melting point(s) (if at least one segment is crystalline), which in turn is based on the desired application, taking into consideration the environment of use. Representative natural polymer blocks or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate), especially poly(3-hydroxybutyrate), poly(3-hydroxyoctanoate), and poly(3-hydroxyfatty acids). Representative natural biodegradable polymer blocks or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein, and copolymers and blends thereof, alone or in combination with synthetic polymers.

Representative synthetic polymer blocks or polymers include polyphosphazenes, polyvinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinyl pyrrolidone, polyesters, polylactides, polyglycolides, polysiloxanes, polyurethanes and copolymers thereof. Examples of suitable polyacrylates include poly(methyl methacrylate), poly(ethyl methacrylate), poly(butyl methacrylate), poly(isobutyl methacrylate), poly(ethylene glycol dimethacrylate) (PEGDMA), diethylene glycol dimethacrylate (DEGDMA), poly(ethylene glycol) diacrylate (PEGDA), poly(hexyl methacrylate), poly(isodecyl methacrylate), poly(lauryl methacrylate), poly(phenyl methacrylate), poly(ethyl acrylate), poly(methyl acrylate), poly(isopropyl acrylate), butyl acrylate, poly(butyl acrylate), poly(tert-butyl acrylate), poly(isobutyl acrylate), poly(isobornyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymer segments include polyhydroxy acids, such as polylactides, polyglycolides and copolymers thereof; poly(ethylene terephthalate); polyanhydrides, poly(hydroxybutyric acid); poly(hydroxyvaleric acid); poly[lactide-co-(ε-caprolactone)]; poly [glycolide-co-(ε-caprolactone)]; polycarbonates, poly (pseudo amino acids); poly(amino acids); poly (hydroxyalkanoate)s; polyanhydrides; polyortho esters; and blends and copolymers thereof. Polymers containing labile bonds, such as polyanhydrides and polyesters, are well known for their hydrolytic reactivity. The hydrolytic degradation rates of these polymer segments can generally be altered by simple changes in the polymer backbone and their sequence structure.

Examples of non-biodegradable synthetic polymer segments include ethylene vinyl acetate, poly(meth)acrylic acid, polyamides, polyethylene, polypropylene, polystyrene, polyvinyl chloride, polyvinylphenol, and copolymers and mixtures thereof. The polymers can be obtained from commercial sources such as Sigma Chemical Co., St. Louis, Mo.; Polysciences, Warrenton, Pa.; Aldrich Chemical Co., Milwaukee, Wis.; Fluka, Ronkonkoma, N.Y.; and BioRad, Richmond, Calif. Alternatively, the polymers can be synthesized from monomers obtained from commercial sources, using standard techniques.

In some implementations, thiol-vinyl and thiol-yne polymer compounds as disclosed in international application no. PCT/US2009/041359 entitled "Thiol-vinyl and thiol-yne systems for shape memory polymers" filed 22 Apr. 2009, which is hereby incorporated by reference herein in its entirety, may be used to form IOLs. In other implementations, polymer formulations may undergo a two-stage curing process in which a second, photo-induced polymerization of still unreacted functional groups is undertaken after an initial cure stage. Such a dual cure system for manufacturing SMP materials is described in U.S. provisional patent application No. 61/410,192 entitled "Dual-cure polymer systems" filed 10 Nov. 2010, which is hereby incorporated by reference herein in its entirety.

In certain embodiments, tert-butyl acrylate (tBA) can be used to impart shape memory properties to SMP materials. Such monomer may be provided in an amount of 50 wt % to 85 wt %, or 60 wt % to 75 wt %, based on total weight of the SMP formulation. Such monomer may be provided in an amount of about 50 wt %, about 55 wt %, about 60 wt %, about 65 wt %, about 70 wt %, about 75 wt %, about 80 wt %, or about 85 wt %, based on total weight of the SMP formulation.

In certain embodiments, n-butyl acrylate (nBA) can be used to modify the glass transition temperature of SMP materials. Such monomer may be provided in an amount of 0 wt % to 20 wt %, 0 wt % to 15 wt %, or 0 wt to 10 wt %, based on total weight of the SMP formulation. Such monomer may be provided in an amount of about 0 wt %, about 5 wt %, about 10 wt %, about 15 wt %, or about 20 wt %, based on total weight of the SMP formulation.

In certain embodiments, 2-hydroxy-3-phenoxypropyl acrylate (HPPA) can be used to increase the refractive index of SMP materials. Such monomer may be provided in an amount of 0 wt % to 20 wt %, 0 wt % to 15 wt %, 0 wt % to 10 wt %, 15 wt % to 20 wt %, or 16 wt % to 18 wt %, based on total weight of the SMP formulation. Such monomer may be provided in an amount of about 0 wt %, about 5 wt %, about 10 wt %, about 15 wt %, or about 20 wt %, based on total weight of the SMP formulation.

Monomers suitable as cross-linkers to prepare SMP materials include, but are not limited to, poly(ethylene glycol) dimethacrylate polymer (PEGDMA), and diethylene glycol. In certain embodiments, the cross-linker is a PEGDMA polymer. The PEGDMA may have a number average molecular weight ($M_n$) ranging from 500 g/mol to 2,000 g/mol. In certain embodiments, the cross-linker is selected from the group consisting of PEGDMA 550, PEGDMA 750, PEGDMA 1000, and PEGDMA 2000, or any combination thereof. In certain embodiments, the cross-linker is PEGDMA 750. In certain embodiments, the cross-linker is PEGDMA 1000.

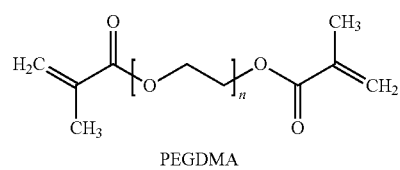

PEGDMA

In certain embodiments, the cross-linker is diethylene glycol.

The cross-linker may be provided in an amount of 3 wt % to 25 wt %, 5 wt % to 20 wt %, or 8 wt % to 12 wt %, based on total weight of the SMP formulation. Such monomers may be provided in an amount of about 5 wt %, about 10 wt %, about 15 wt %, about 20 wt %, or about 25 wt %, based on total weight of the SMP formulation.

Monomers suitable as UV-blockers for inclusion in SMP materials include, but are not limited to, benzophenones and benzotriazoles. In certain embodiments, the UV-blocker is selected from the group consisting of a methacryloyl chlorobenzotriazole, a methacryloyl methoxybenzotriazole, and a yellow dye, or any combination thereof. Suitable methacryloyl chlorobenzotriazoles include 2-methylacrylic acid 3-[3-tert-butyl-5-(5-chlorobenzotriazol-2-yl)-4-hydroxyphenyl]-propyl ester (UVB), and 2-(2-hydroxy-3-tert-butyl-5-vinylphenyl)-5-chloro-2H-benzotriazole (UVAM). A suitable methacryloyl methoxybenzotriazole is 3-(tert-butyl)-4-hydroxy-5-(5-methoxy-2H-benzo[d][1,2,3]triazol-2-yl) phenethyl methacrylate. A suitable yellow dye is (E)-2-(2-cyano-3-(4-(1,1-dioxidothiomorpholino)phenyl) acrylamido)ethyl methacrylate).

Preferred UV blockers include the benzotriazole class of compounds. Benzotriazoles are generally more efficient at blocking UV than are benzophenones. In certain embodiments, chlorobenzotriazoles are preferred, and in particular, chlorobenzotriazoles polymerizable by free radical mechanisms. In certain embodiments, methoxybenzotriazoles are preferred, and in particular, methoxybenzotriazoles polymerizable by free radical mechanisms. Particularly preferred UV blockers include methacrylate-functional chloro-substituted benzotriazoles and methacrylate-functional methoxy-substituted benzotriazoles.

Chlorobenzotriazoles and methoxybenzotriazoles exhibit a maximum absorbance at higher wavelengths than standard benzotriazoles. The chloro-substitution and methoxy-substitution shift the peak absorption of the molecule toward the visible range (e.g., closer to 400 nm). The higher UV-blocking efficiency, combined with the shift of the peak absorbance wavelength, may allow incorporation of such UV benzotriazole blockers at lower concentrations compared to benzophenones, while producing effective filtration of the entire UV spectrum (e.g., up to 400 nm).

In certain embodiments, a combination of benzotriazole UV-blockers may be used. For example, a standard benzotriazole UV-blocker may be used to block a lower wavelength portion of the UV spectrum (having a lower peak absorbence) and a chloro-substituted and/or methoxy-substituted benzotriazole may be used to block a higher wavelength portion of the UV spectrum (e.g., closer to 400 nm).

The methacrylate functionality of the UV-blockers may be beneficial to the SMP formulation compared to vinyl- allyl- or other functionality, as the methacrylate functionality may provide suitable reaction kinetics for monomer incorporation into a shape memory polymer, particularly where the other monomers (e.g., cross-linkers) include methacrylate functionalities as the polymerizable functional group.

In certain embodiments, yellow dyes are beneficial to the formulation as a means to filter the violet range of the visible light spectrum. Methoxybenzotriazoles may be an alternative to yellow dyes.

Suitable UV-blockers are shown in Table 1.

TABLE 1

| UV Blocker | Structure | CAS # |
| --- | --- | --- |
| Methacryloyl Chlorobenzotriazole | 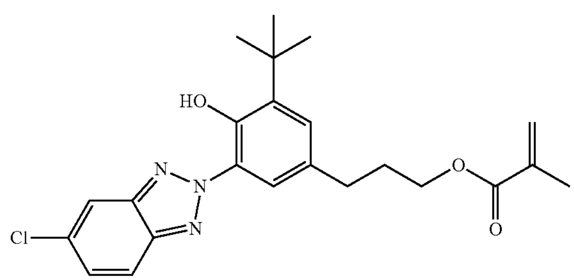 [SMILES: C=C(C)C(=O)OCCCc1cc(-n2nc3ccc(Cl)cc3n2)c(O)c(C(C)(C)C)c1] | 96478-15-8 |
| UVAM | 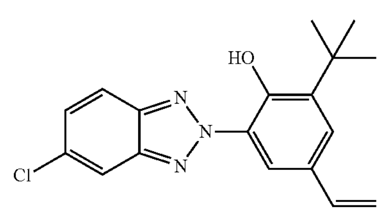 [SMILES: C=Cc1cc(-n2nc3ccc(Cl)cc3n2)c(O)c(C(C)(C)C)c1] | 124883-10-9 |
| Yellow Dye | 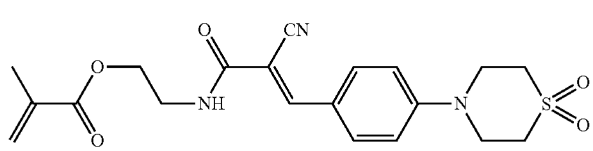 [SMILES: C=C(C)C(=O)OCCNC(=O)/C(C#N)=C/c1ccc(N2CCS(=O)(=O)CC2)cc1] | N/A |

TABLE 1-continued

| UV Blocker | Structure | CAS # |
|---|---|---|
| Methacryloyl Methoxybenzotriazole | 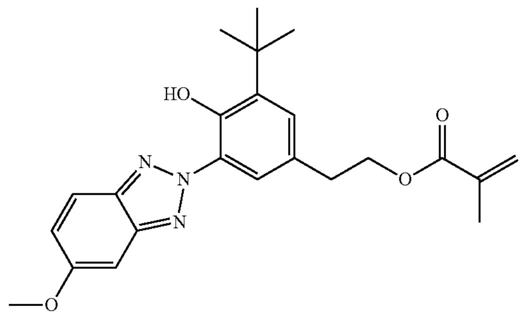 [SMILES: C=C(C)C(=O)OCCc1cc(-n2nc3ccc(OC)cc3n2)c(O)c(C(C)(C)C)c1] | N/A |

The UV-blocker may be provided in an amount of 0.2 wt % to 2 wt %, 0.25 wt % to 1.5 wt %, or 0.5 wt % to 1 wt %, based on total weight of the SMP formulation. Such monomers may be provided in an amount of about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, or about 1.5 wt %, based on total weight of the SMP formulation.

Manufacturing of SMP IOLs may be achieved through either thermal initiation, photoinitiation, or a combination of the two processes. Monomers suitable as polymerization initiators include, but are not limited to, 2,2-dimethoxy-2-phenylacetophenone (Irgacure 651), phenylbis(2,4,6-trimethylbenzoyl) phosphine oxide (Irgacure 819), azobisisobutyronitrile (AIBN), lauroyl peroxide, di(4-tert-butylcyclohexyl) peroxydicarbonate (Perkadox 16), camphorquinone, and diphenyl-(2,4,6-trimethylbenzoyl)-phosphine oxide (TPO). In certain embodiments, the polymerization initiator is lauroyl peroxide. Thermal and photo initiators that may be used for the formulations are listed in Table 2.

TABLE 2

| Initiator | Structure | CAS # |
|---|---|---|
| Lauroyl Peroxide | 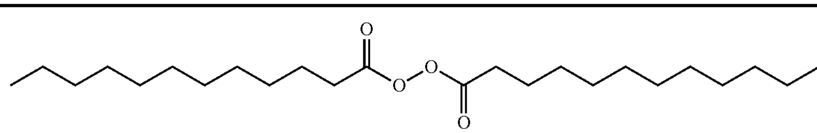 | 105-74-8 |
| 2,2'-Azobis(2-methylpropionitrile) (AIBN) | 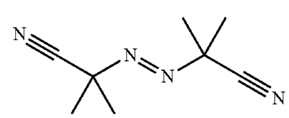 | 78-67-1 |
| Di(4-tert-butylcyclohexyl) peroxydicarbonate (Perkadox 16) | 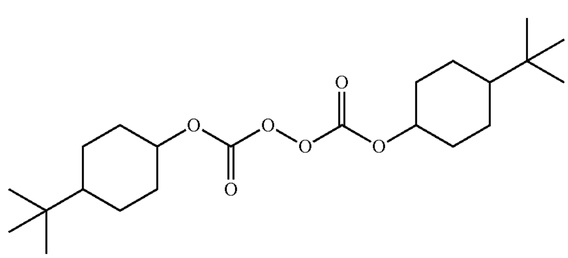 [SMILES: CC(C)(C)C1CCC(OC(=O)OOC(=O)OC2CCC(C(C)(C)C)CC2)CC1] | 15520-11-3 |
| Phenylbis(2,4,6-trimethylbenzoyl) phosphine oxide (Irgacure 819) | 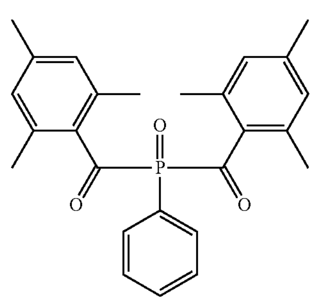 [SMILES: Cc1cc(C)c(C(=O)P(=O)(C(=O)c2c(C)cc(C)cc2C)c2ccccc2)c(C)c1] | 162881-26-7 |

TABLE 2-continued

| Initiator | Structure | CAS # |
|---|---|---|
| 2,2-Dimethoxy-2-phenylacetophenone (Irgacure 651) | 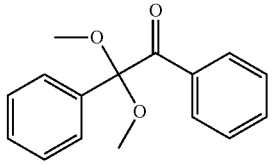 [SMILES: COC(OC)(C(=O)c1ccccc1)c1ccccc1] | 24650-42-8 |
| Camphorquinone | 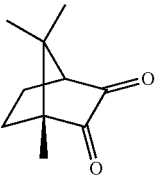 | 10373-78-1 |
| Diphenyl-(2,4,6-trimethylbenzoyl)-phosphine oxide (TPO) | 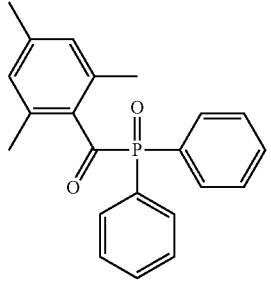 [SMILES: Cc1cc(C)c(C(=O)P(=O)(c2ccccc2)c2ccccc2)c(C)c1] | 75980-60-8 |

In certain embodiments, the shape memory polymer formulation may be polymerized using a photoinitiator. For example, the shape memory polymer formulation may be polymerized using Irgacure 651 as a photoinitiator, preferably when UV-blockers are absent in the formulation. The shape memory polymer formulation may be polymerized using Irgacure 819 as a photoinitiator, preferably when UV-blockers are present in the formulation. Irgacure 819 is capable of absorbing light into the visible range, allowing it to remain effective as a photoinitiator when mixed with competing UV absorbing components.

In certain embodiments, the shape memory polymer formulation may be polymerized using a thermal initiator. For thermal initiation, both peroxides and azo initiators may be utilized. Suitable thermal initiators include, but are not limited to, AIBN, lauroyl peroxide, and Perkadox 16. Thermal initiators may be preferred when fabricating IOLs via cryolathing.

In certain embodiments, a dual initiation system (photo and thermal curing) may be used to affect polymerization of the shape memory polymer formulation. The formulation may be initially cured by photoinitiation in order to quickly gel the polymer. The polymerization reaction may be driven to completion (high monomer-to-polymer conversion) by either continued photoinitiation or by thermal initiation. The thermal initiation may be driven as a separate process in which the polymer is transferred to a hot oven or bath.

In certain embodiments, the addition of a mix of photo and thermal initiators may drive a simultaneous mechanism. For example, irradiation of a monomer formulation with light (UV or visible) may initiate polymerization by photochemical reaction. The exothermic nature of the free radical polymerization may induce further polymerization via a thermal mechanism. A more reactive thermal initiator such as Perkadox 16 may be preferred for such a dual initiation system.

The initiator may be provided in an amount of 0.01 wt % to 5 wt %, 0.05 wt % to 3 wt %, 0.05 wt % to 1 wt %, 0.1 wt % to 0.5 wt %, or 0.1 wt % to 0.2 wt %, based on total weight of the SMP formulation. The initiator may be provided in an amount of about 0.01 wt %, about 0.05 wt %, about 0.10 wt %, about 0.15 wt %, about 0.20 wt %, about 0.25 wt %, about 0.30 wt %, about 0.35 wt %, about 0.40 wt %, about 0.45 wt %, about 0.5 wt %, about 1 wt %, about 2 wt %, or about 3 wt %, based on total weight of the SMP formulation. Formulations vary in quantity of initiator to optimize cycle time during the manufacturing process and still maintain desired thermomechanical properties.

In certain embodiments, a colorant may be added to the SMP formulations. SMP materials with SPECTRAFLO (trademark of Ferro) liquid may be prepared. The formulations may include 0.1 wt % to 2 wt % colorant, based on total weight of the SMP formulation. Various colors may be added while maintaining desired thermomechanical properties.

In certain embodiments, a SMP material or network may include dissolving materials which may include part of the network or may be included in the formulation of the network before the network is polymerized (e.g., as an aggregate, mixed into the formulation). Dissolving materials may include materials that disperse over time, even if the material or part of the material does not actually dissolve or enter into a solution with a solvent. In other words, a dissolving material as used herein may be any material that may be broken down by an anticipated external environment of the polymer. In one embodiment, a dissolving material is a drug which elutes out of a SMP network. A dissolving material may be attached by chemical or physical bonds to the polymer network and may become disassociated with the polymer network over time.

Dissolving materials, through their dissolution over time, may be used for many purposes. For example, the dissolution of a material may affect a dissolution or break-up of a biomedical device over time. Alternatively, the dissolution of a material may elute a drug, achieving a pharmacological purpose. Medications or drugs can be infused into SMP devices to aid in healing (e.g., anti-inflammatory), avoid complications (e.g., anti-thrombotic), or to combat potential infection (e.g., antibiotic). Medications may be added by injection into the liquid polymer before curing. Medications may also be added to SMP devices post-polymerization using various surface modification or coating techniques, for example, plasma deposition.

Exemplary SMP Formulations

Some exemplary SMP formulations and their measured properties are reported in Table 3 below. In one formulation, tert-butyl acrylate (tBA) is combined with poly(ethylene glycol) dimethacrylate (PEGDMA) 1000 as a cross-linker. The weight percentages of each may be varied to design an SMP with particular desired material properties.

TABLE 3

| Formulation | Tg (° C.) | Rubbery Modulus (MPa) | RI | Max Tensile Strain (%) | Compressive Strain (%) | Glistening Properties |
|---|---|---|---|---|---|---|
| tBa (78%); PEGDMA 1000 (22%) | 40 | 2.5 | 1.465 | >250 | >65 | Glistening Free |
| tBA (65%); nBA (13%); PEGDMA 1000 (22%) | 25 | 2.5 | 1.475 | >125 | >65 | Glistening Free |
| tBA (50%); isobutyl acrylate (28%); PEGDMA 1000 (22%) | 17 | 2.5 | 1.468 | >100 | >65 | Glistening Free |

As one example of the optimization, recovery time is controlled by the relationship of the glass transition temperature (Tg) of the SMP material used to the environmental temperature (Te) in which an SMP device is deployed. A Tg<Te deploys more slowly than a Tg=Te, and a Tg>Te deploys at the fastest rate. Tg of the material may be controlled from −35° C. up to 114° C., allowing a wide range of control over the deployment rate into the body. Desirable ranges for Tg in IOL devices may be between 10° C. and 60° C., and even more desirably between 15° C. and 45° C. Devices have been created that deploy in less than a second all the way up to several minutes to fully deploy.

The ability to change refractive index has also been investigated through changes to the SMP formulation. Table 4 below provides data on the refractive index of the different components used in several exemplary formulations.

TABLE 4

| Chemical Name | Refractive Index @ 36° C. | Functionality |
|---|---|---|
| tert-Butyl Acrylate (tBA) | 1.4031 | Monomer |
| Poly(ethylene glycol) dimethylacrylate (PEGDMA) 550 | 1.4609 | Cross-linker |
| Poly(ethylene glycol) dimethylacrylate (PEGDMA) 1000 | 1.460 | Cross-linker |
| Polycarbonate (PC) Diacrylate 610 | 1.4635 | Cross-linker |
| KIFDA 542 (King Industries, Inc., Norwalk, CT) | 1.475 | Cross-linker |

TABLE 4-continued

| Chemical Name | Refractive Index @ 36° C. | Functionality |
|---|---|---|
| Bisphenol A propoxylate diacrylate (BPA-P) Diacrylate | 1.515 | Cross-linker |
| Poly(ethylene glycol) diacrylate (PEGDA) 575 | 1.467 | Cross-linker |
| Poly(ethylene glycol) diacrylate (PEGDA) 700 | 1.47 | Cross-linker |

While certain molecular weights of the cross-linkers are presented with measured refractive indexes in Table 4, other molecular weights can be uses in varying formulations. For example, poly(ethylene glycol) diacrylate (PEGDA), poly(ethylene glycol) diacrylate (PEGDA) may be used with good result in various molecular weights of between 500 and 2000.

SMP samples listed in Table 5 below were created and the refractive indices were measured. Cross-linking of 20% for the noted cross-linker polymer was used. The results show only slight changes to the refractive index values based on the formulations created. Increasing the content of the cross-linker in the formulations may be used to change the refractive index values more. In addition, other formulations may be prepared with poly(carbonate) diacrylate, KIFDA-542 diacrylate (available from King Industries, Inc., Norwalk, Conn.), and bisphenol-A propoxylate diacrylate that have a greater effect on changing the refractive index.

TABLE 5

| Formulation | Tg (° C.) | RI | Glistening Evaluation |
|---|---|---|---|
| tBA (80%):PEGDMA 550 (20%) | 52 | 1.465 | glistens |
| tBA (64%):nBA (24%):PEGDMA 550 (12%) | 32 | | glistens |
| tBA (78%):PEGDMA 1000 (22%) | 40 | 1.465 | does not glisten |
| tBA (60%):nBA (20%):PEGDMA 550 (20%) | 30 | | glistens |
| tBA (56%):nBA (14%):PEGDMA 550 (30%) | 32 | | glistens |
| tBA (80%):PC-DA (20%) | 59 | 1.463 | glistens |
| tBA (78%):SR601 (22%) | 71 | 1.48 | does not glisten |
| tBA (78%):SR602 (22%) | 52 | 1.478 | does not glisten |
| tBA(78%):CD9038 (22%) | 41 | 1.468 | does not glisten |
| tBA (65%):nBA (13%):PEGDMA 1000 (22%) | 25 | 1.475 | does not glisten |
| tBA (78%):PEGDMA 1000 (22%):BTA (.5%) | 40 | 1.465 | does not glisten |
| tBA (78%):PEGDMA 1000 (22%):BTA (1%) | 40 | 1.465 | does not glisten |
| isobutylA (78%):PEGDMA 1000 (22%) | −13.5 | | |
| nBA (78%):PEGDMA 1000 (22%) | −27.5 | | |
| tBA (50%):isobutylA (28%):PEGDMA 1000 (22%) | 17.5 | 1.468 | does not glisten |
| HPPA (78%):PEGDMA 1000 (22%) | 23 | 1.542 | does not glisten |
| HPMAEP (78%):PEGDMA 1000 (22%) | 34 | 1.536 | does not glisten |
| tBA (60%):PEGDMA 1000 (40%) | 18 | | does not glisten |
| tBA (76%):isobutylA (14%):PEGDMA 1000 (10%) | 43 | | |
| tBA (85%):PEGDMA 1000 (15%) | 48 | | |

The ability to change light transmission properties through the SMP materials has been investigated. 2-[3-(2H-Benzotriazol-2-yl)-4-hydroxyphenyl]ethyl methacrylate (BTA) was added to the SMP IOL formulation as an ultraviolet (UV) wavelength blocker, as indicated in the table above. Two formulations with 0.5% UV blacker and 1% UV blocker were created and then analyzed for UV through visible wavelength transmission and dynamic mechanical analysis. FIG. 1 is a graph showing the storage modulus and the tan delta (the ratio of the storage modulus to the loss modulus) of the following three material formulations over a range of temperatures from 0 to 100° C.:

SMP106: 78% tBA and 22% PEGDMA 1000 with no UV blocker;

SMP122: SMP106 with 0.5 weight % BTA functionalized UV blocker added; and

SMP123: SMP106 with 1.0 weight % BTA functionalized UV blocker added.

The upper curve is the storage modulus and the lower curve is the tan delta. As is apparent, the addition of the small amounts of BTA as a UV blocker has little if any effect on the modulus of the SMP materials and the Tg (the peak of the tan delta curve) is constant for all three formulations.

Figure 2:
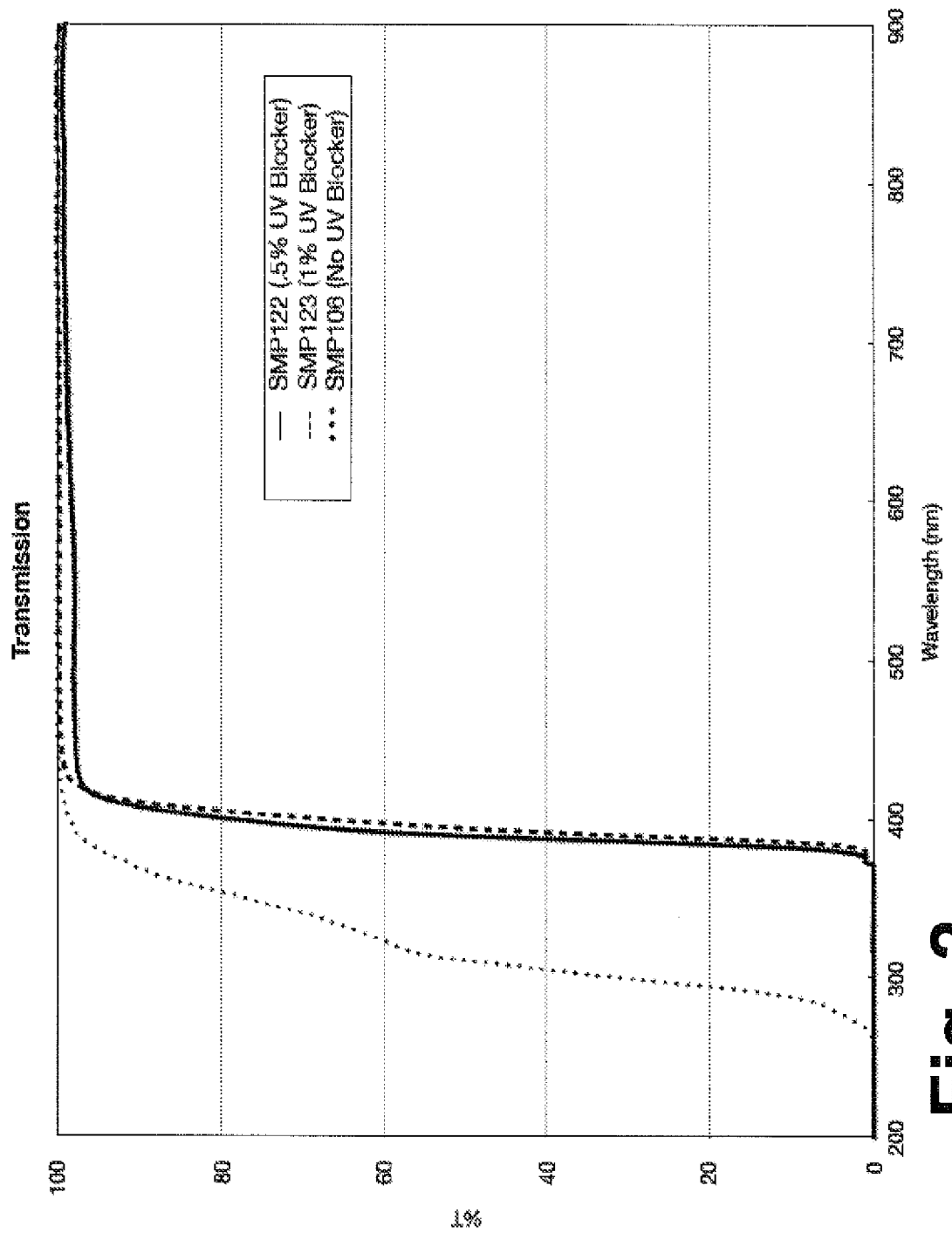
FIG. 2 is a graph depicting the UV blocking properties and optical clarity of the exemplary SMP formulations of FIG. 9 as a percentage of transmission over a range of wavelengths in the UV and visible spectrum.

FIG. 2 shows the effect of the addition of the BTA UV blocker on the SMP materials of FIG. 1. As is apparent, the addition of the UV blocker has negligible effect on light transmission in the visible wavelengths, but sharply attenuates wavelengths below about 380 nm, which is the upper end of the UV spectrum.

Figure 3:
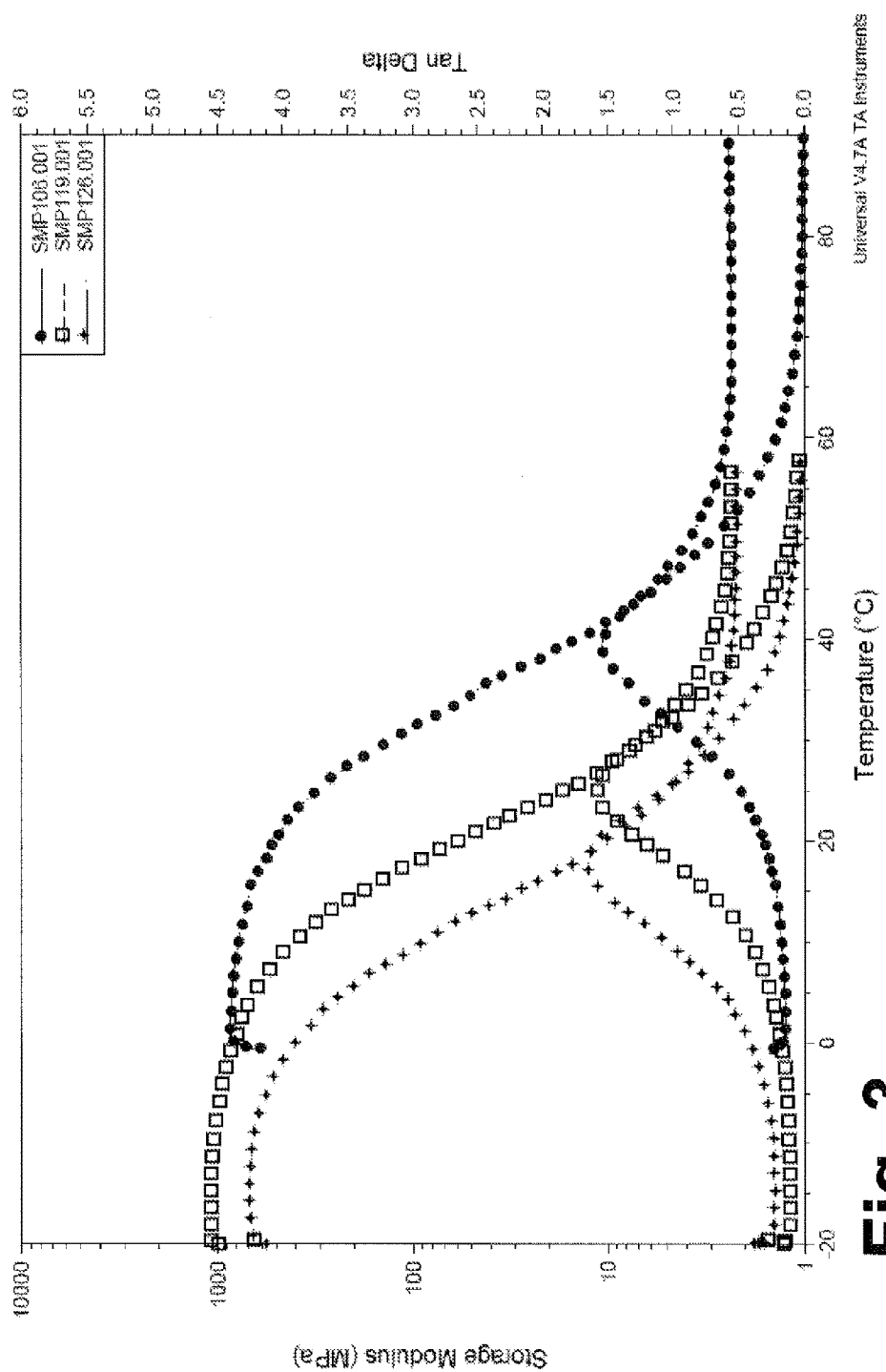
FIG. 3 is a graph depicting the storage modulus vs. temperature attributes for several exemplary SMP formulations.

FIG. 3 is a graph showing the storage modulus and the tan delta of two additional SMP formulations over a range of temperatures from −20 to 100° C. in comparison to SMP106:

SMP119: 65 wt % tBA, 13 wt % butyl acrylate, 22 wt % PEGDMA 1000; and

SMP126: 50 wt % tBA, 28 wt % isobutyl acrylate, 22 wt % PEGDMA 1000.

The upper curve is the storage modulus and the lower curve is the tan delta. The difference in formulas provides different Tg for use in different environments and for different applications in which it may be useful to have a lower transition temperature. SMP119 has a Tg of about 25° C. and SMP126 has a Tg of about 17° C. However, even with the differences in Tg, the storage moduli of the SMP119 and SMP126 formulations compare favorably to the SMP106 material.

Figure 4:
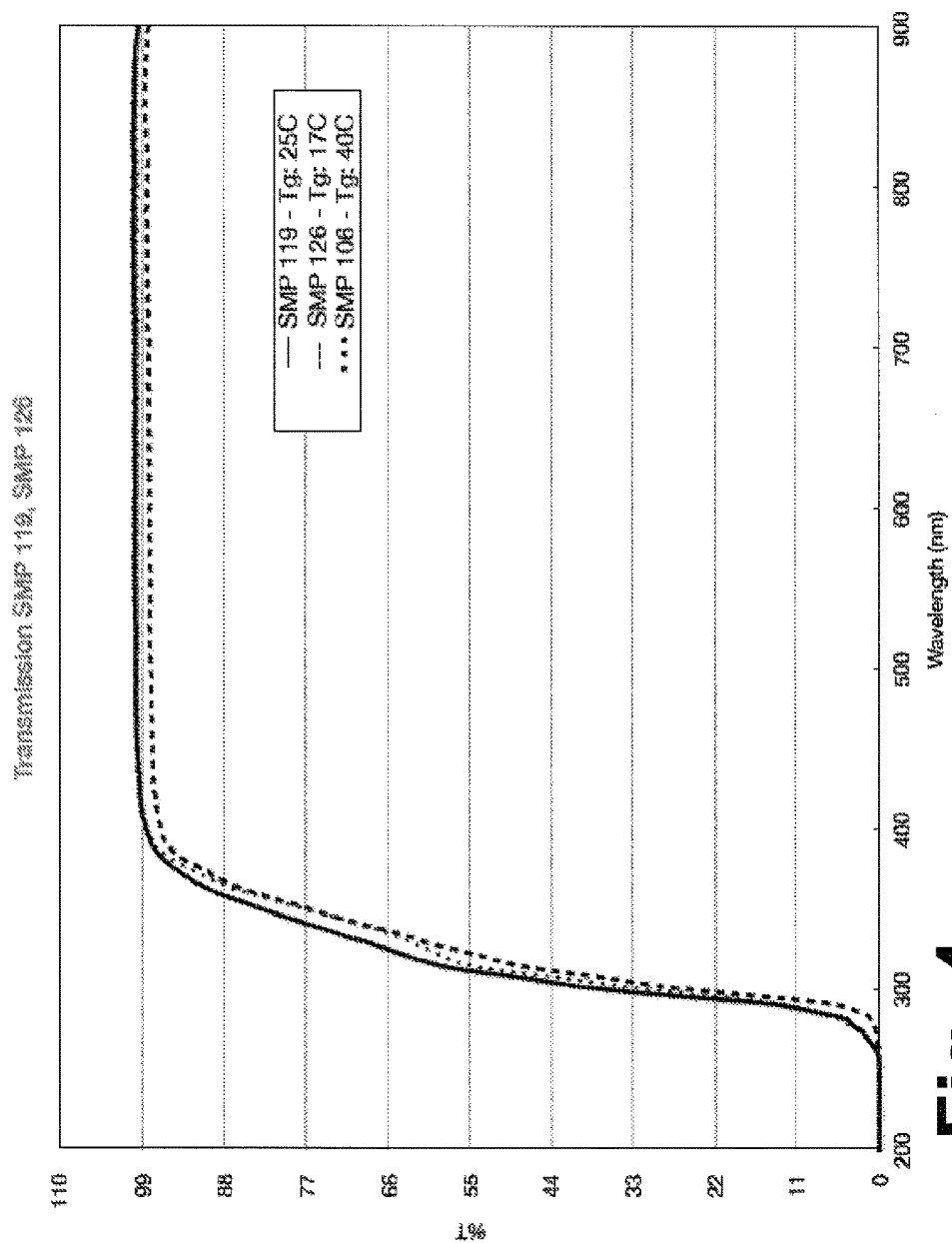
FIG. 4 is a graph depicting the UV blocking properties and optical clarity of the exemplary SMP formulations of FIG. 11 as a percentage of transmission over a range of wavelengths in the UV and visible spectrum.

FIG. 4 also indicates that the light transmission properties of SMP119 and SMP126 compare favorably to the SMP106 formula.

Figure 5:
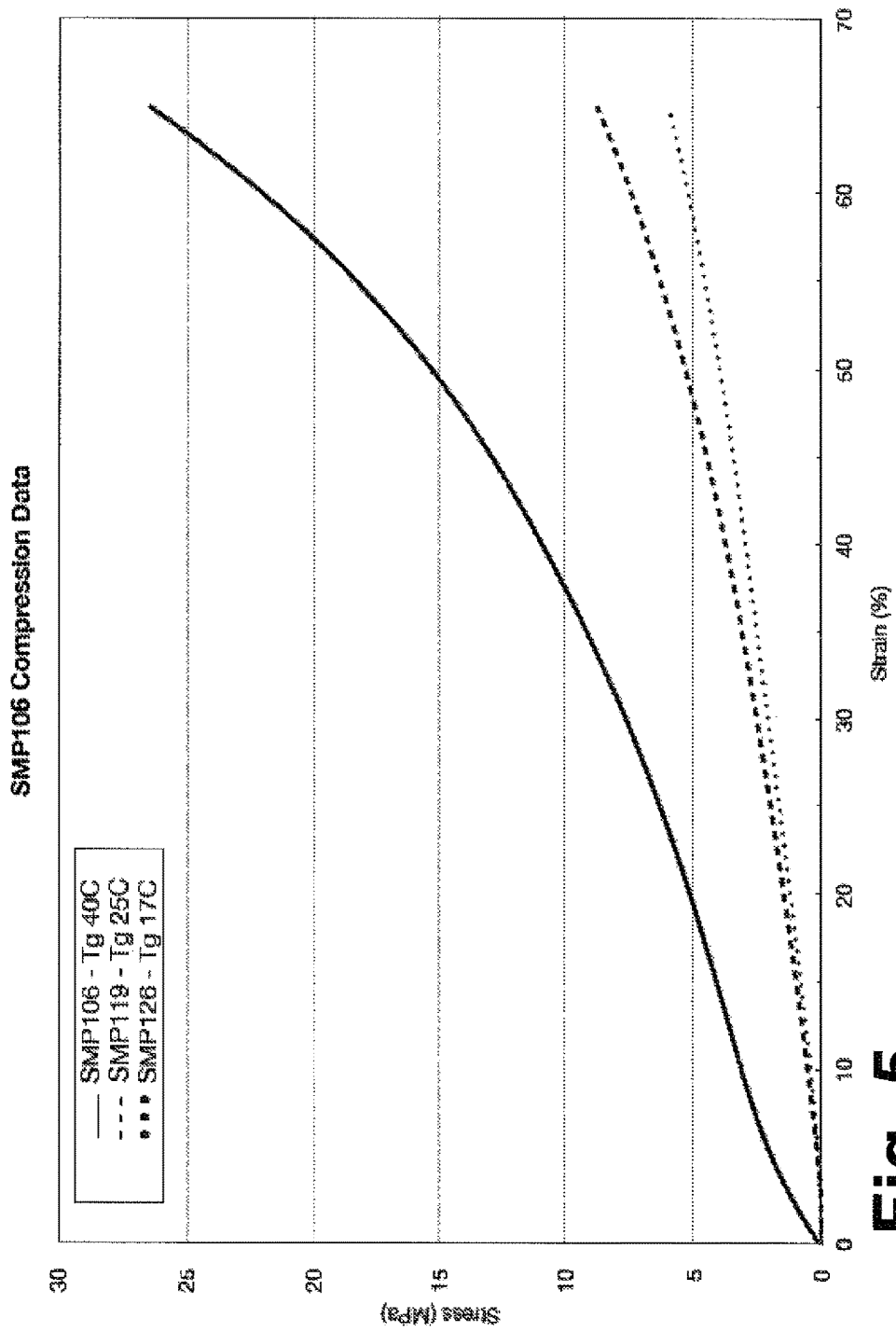
FIG. 5 is a graph depicting the compression properties of the exemplary SMP formulations of FIG. 11.
Figure 6:
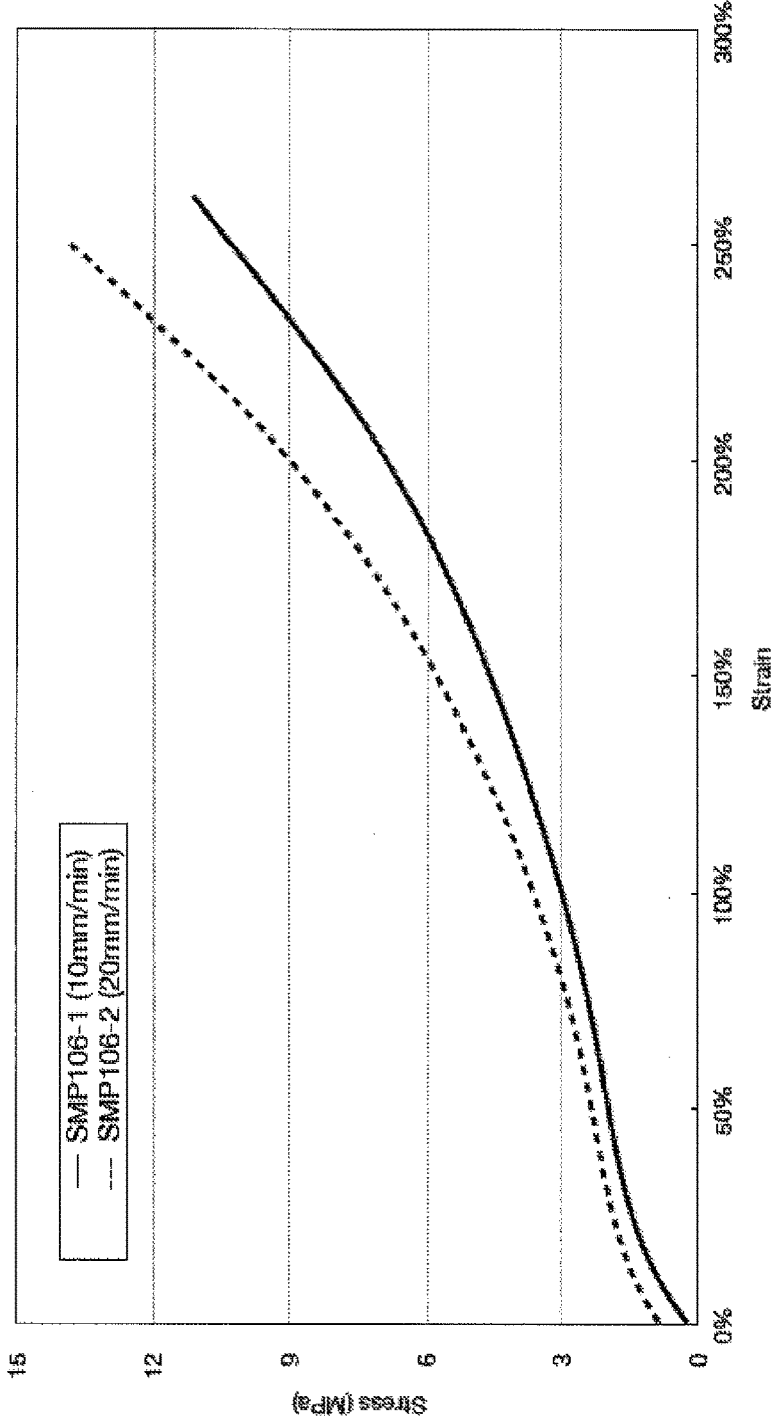
FIG. 6 is a graph depicting the tensile properties of an exemplary SMP formulation at two different rates of strain.

FIG. 5 is a graph depicting stress-strain data curves for SMP106, SMP119, and SMP126 for the materials under compression. As is apparent, the SMP119 and SMP126 formulas exhibit significantly less stress under a compressive strain of 65% compared to the SMP106 formula. This allows these materials to be more easily deformed at lower temperatures, such as room temperature. FIG. 6 is another stress-strain curve for SMP106 for two separate rates of elongation under tension, i.e., for rates of 10 mm/min and 20 mm/min. As shown in the graph, SMP106 performs quite well under tension and withstood up to and over 250% strain at both rates.

SMP106 was used as the basis for the development of additional formulations including UV-blockers. Initially, 2-methylacrylic acid 3-[3-tert-butyl-5-(5-chlorobenzotriazol-2-yl)-4-hydroxyphenyl]-propyl ester (UVB) and 2-(2-hydroxy-3-tert-butyl-5-vinylphenyl)-5-chloro-2H-benzotriazole (UVAM) were each incorporated into the SMP106 formulation at 0.5 wt %, 1.0 wt % and 2.0 wt % to determine the amount needed to achieve 10% transmission (T) cut-off at 400 nm. UV/Vis transmission was run on samples containing each of these blockers. Due to the addition of the UV blockers and the absorption spectrum of DMPA, the initiator was switched to a compound that absorbs in the visible spectrum. Bis(2,4,6-trimethylbenzoyl)-phenylphosphineoxide (IRGACURE 819) was chosen due to its absorption characteristics in the visible range above 400 nm. The results are shown in Table 6.

TABLE 6

| Formulation | % Transmission at 400 nm |
| --- | --- |
| SMP208: tBA(77.5%):UVB(0.5%):PEGDMA1000(22%):IRGACURE819(0.15%) | 14.20 |
| SMP209: tBA(77.0%):UVB(1.0%):PEGDMA1000(22%):IRGACURE819(0.15%) | 2.39 |
| SMP210: tBA(76.0%):UVB(2.0%):PEGDMA1000(22%):IRGACURE819(0.15%) | 0.37 |
| SMP211: tBA(77.5%):UVAM(0.5%):PEGDMA1000(22%):IRGACURE819(0.15%) | 10.39 |
| SMP212: tBA(77.0%):UVAM(1.0%):PEGDMA1000(22%):IRGACURE819(0.15%) | 1.59 |
| SMP213: tBA(76.0%):UVAM(2.0%):PEGDMA1000(22%):IRGACURE819(0.15%) | 0.03 |

Based on the results from this initial data, a linear fit was used to determine the amount of each UV blocker needed to achieve the 10% T cut-off at 400 nm. This was determined to be 0.7 wt % of the UVB blocker and 0.55 wt % of the UVAM blocker. The following high Tg and low Tg formulations were created with these blocker amounts, as shown in Table 7.

TABLE 7

| Formulation | % Transmission at 400 nm | Tg (° C.) |
|---|---|---|
| SMP214: tBA(77.3%):UVB(0.7%):PEGDMA1000(22%):IRGACURE819(0.15%) | 6.37 | 41 |
| SMP215: tBA(77.45%):UVAM(0.55%):PEGDMA1000(22%):IRGACURE819(0.15%) | 9.30 | 41 |
| SMP218: tBA(64.30%):nBA(13.0%):UVB(0.7%):PEGDMA1000(22%):IRGACURE819(0.15%) | 6.28 | 25 |
| SMP219: tBA(64.45%):nBA(13.0%):UVAM(0.55%):PEGDMA1000(22%):IRGACURE819(0.15%) | 7.79 | 25 |

Polymerization Parameters and Coupon Preparation for Formulations 214, 215, 218, and 219

Liquid monomer solutions of the 214, 215, 218 and 219 formulations were created by mixing the individual monomer components. A 20 ml scintillation vial was placed on a balance with 0.1 mg resolution. The individual monomer components were added to the vial in the specified amounts. Lastly the initiator was added and the vials were wrapped in foil to protect the mixture from light. The monomer solutions were mixed on a heated stir plate at 45° C. and 500 rpm for 20 minutes. Each formulation was then visually inspected to ensure complete mixing of the components. The formulations were stored protected from light until used for polymerization.

Light polymerization was used to cure all polymer samples. The liquid monomer solutions were injected in between two glass microscope slides spaced 1 mm apart. The glass slides were treated with glassclad 18. The slides were exposed to 320-500 nm collimated light at 40 mW/cm$^2$ for 10 mins, flipped and the bottom side was exposed for an additional 10 minutes. Upon completion of photo-curing the polymer samples were set in an oven at 90° C. for 1 hour. Upon completion of the heat treatment, the polymer slides were removed from the molds and allowed to cool.

Figure 15:
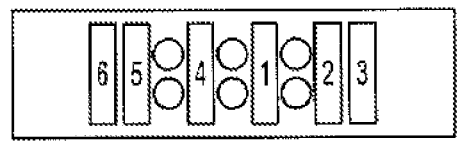
FIG. 15 is a picture of a polymer slide with a coupon cutting diagram overlayed.

Two polymer slides of each formulation were produced. The slides were then cut as shown in FIG. 15. In order to meet the requirements for the refractive index measurements, larger samples 20 mm×8 mm×3 mm were created specifically for this test using the same polymerization conditions.

Transmission Tests for Formulations 214, 215, 218 and 219

Figure 16:
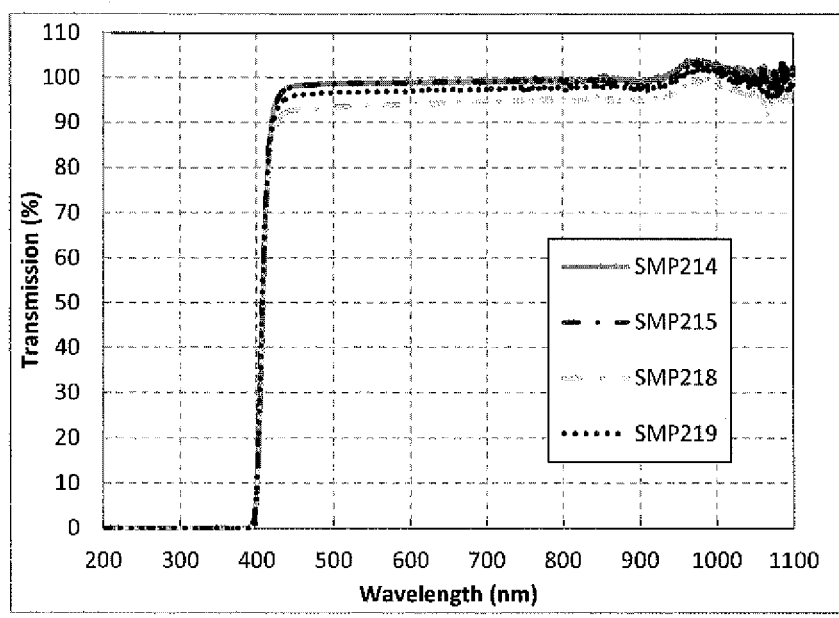
FIG. 16 is a transmission spectrum of SMP 214, 215, 218, and 219 (1.0 mm thick).

Polymer coupons 1 mm thick of each formulation 214, 215, 218 and 219 were placed in a custom sample holder and inserted into a quartz cuvette. The cuvette was filled with distilled water and placed in the UV-Vis spectrophotometer. Four coupons of each formulation from two different slides were measured in transmission mode. The samples were scanned from 190 nm-1100 nm at 1 nm resolution. The transmission data for all four systems is given in Table 8. One transmission curve for each formulation is shown in FIG. 16.

TABLE 8

| Wavelength (nm) | Average Transmission (n = 4) | | | |
|---|---|---|---|---|
| | SMP214 | SMP215 | SMP218 | SMP219 |
| 300 | 0.00 ± 0.01 | 0.00 ± 0.01 | 0.02 ± 0.00 | 0.00 ± 0.01 |
| 365 | 0.01 ± 0.01 | 0.02 ± 0.03 | 0.03 ± 0.02 | 0.00 ± 0.02 |
| 400 | 6.37 ± 0.28 | 9.30 ± 0.31 | 6.28 ± 0.16 | 7.79 ± 0.38 |
| 440 | 97.53 ± 0.19 | 97.24 ± 0.32 | 94.43 ± 1.54 | 93.75 ± 1.12 |
| 600 | 98.96 ± 0.16 | 98.80 ± 0.35 | 95.85 ± 1.49 | 95.72 ± 0.94 |
| 800 | 99.13 ± 0.24 | 99.00 ± 0.25 | 96.51 ± 1.40 | 96.54 ± 0.69 |

Refractive Index and EWC of Formulations 214, 215, 218, 219, and 230b

Formulations 214, 215, 218 and 219 exhibited great incorporation of the UV blocker; however the low refractive index (RI) and high equilibrium water content (EWC) of these materials necessitated additional formulations. Table 9 provides an overview of the RI and EWC values for these formulations and an additional formulation, SMP230. In order to increase the RI, 2-hydroxy-3-phenoxypropyl acrylate (HPPA) was incorporated into the system. Additionally, the hydrophilic PEGDMA1000 content was scaled back in an effort to decrease the EWC. The UVB blocker was chosen due to its increased reactivity from the methacrylate functionality compared to the UVAM monomer. Table 10 outlines the SMP230b formulation.

TABLE 9

| Formulation | RI (Hydrated at 35° C.) | EWC (%) at 35° C. |
|---|---|---|
| SMP214 | 1.4597 | 7.82 |
| SMP215 | 1.4574 | 7.78 |
| SMP218 | 1.4589 | 7.75 |
| SMP219 | 1.4584 | 8.08 |
| SMP230 | 1.4709 | 1.66 |

TABLE 10

| ID | Formulation |
|---|---|
| SMP230b | tBA(59.80%):nBA(12.00%):HPPA(17.50%):UVB(0.70%):PEGDMA1000(10%):LP(0.15%) |

Polymerization Parameters and Coupon Preparation for Formulations 230b

Liquid monomer solutions of the SMP230b formulation were created by mixing the individual monomer components. A 20 ml scintillation vial was placed on a balance with 0.1 mg resolution. The individual monomer components were added to the vial in the specified amounts. Lastly the initiator was added and the vials were wrapped in foil to protect the mixture from light. Each formulation was then visually inspected to ensure complete mixing of the components. The formulations were stored protected from light and heat until used for polymerization.

Thermal polymerization using Lauroyl Peroxide (LP) was used to cure the polymer samples. The liquid monomer solutions were injected between two glass microscope slides spaced either 0.7 mm or 1.4 mm apart. Viton was used for the gasket due to its working temperature range. The formulations were cured in the mold in a water bath at 80° C. for 2 hours and then transferred to an oven to cure for an additional 2 hours at 90° C. The degree of polymerization was monitored at specified intervals using FTIR to measure double bond conversion. Upon completion of the polymerization, the polymer samples were removed from the molds and allowed to cool.

Transmission Tests for Formulation 230b

Figure 17:
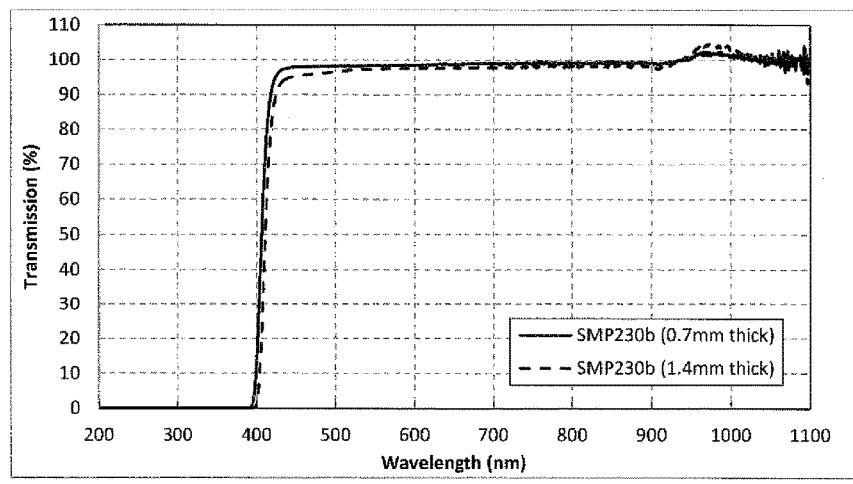
FIG. 17 is a transmission spectrum of SMP230b (0.7 mm thick and 1.4 mm thick).

Polymer coupons 0.7 mm thick and 1.4 mm thick of the SMP230b formulation were placed in a custom sample holder and inserted into a quartz cuvette. The cuvette was filled with distilled water and placed in the UV-Vis spectrophotometer. Three coupons were measured in transmission mode. The samples were scanned from 190-1100 nm at 1 nm resolution. The transmission data for the samples are given in Table 11 (light transmittance of Sample A (sa) at 0.7 mm thick) and Table 12 (light transmittance of Sample B (sb) at 1.4 mm thick). One transmission curve for each thickness is shown in FIG. 17.

TABLE 11

| Wavelength | SMP230b-sa_01 | SMP230b-sa_02 | SMP230b-sa_03 | Average | Std Dev |
|---|---|---|---|---|---|
| 800 | 98.78 | 97.66 | 98.83 | 98.43 | 0.66 |
| 600 | 98.39 | 97.60 | 98.02 | 98.01 | 0.40 |
| 440 | 97.71 | 96.53 | 96.58 | 96.94 | 0.67 |
| 400 | 12.46 | 11.92 | 12.13 | 12.17 | 0.27 |
| 365 | −0.01 | 0.02 | 0.02 | 0.01 | 0.02 |
| 300 | 0.00 | 0.01 | 0.01 | 0.01 | 0.01 |

TABLE 12

| Wavelength | SMP230b-sb_01 | SMP230b-sb_02 | SMP230b-Sb_03 | Average | Std Dev |
|---|---|---|---|---|---|
| 800 | 98.02 | 95.88 | 97.90 | 97.27 | 1.21 |
| 600 | 97.44 | 94.91 | 97.25 | 96.54 | 1.41 |
| 440 | 94.81 | 92.87 | 95.47 | 94.39 | 1.35 |
| 400 | 1.17 | 1.02 | 1.27 | 1.16 | 0.13 |
| 365 | 0.02 | 0.02 | 0.01 | 0.02 | 0.01 |
| 300 | 0.01 | 0.01 | 0.00 | 0.01 | 0.00 |

Refractive Index and EWC of SMP230 Formulations

An Abbe refractometer was used to make RI measurements for formulation 230. Polymer coupons of each formulation were polymerized as described above and 6 mm diameter buttons were cut for the testing. The polymer sample was placed on the refractometer prism and allowed to acclimate to temperature for 1 minute. The RI value was measured and recorded. The RI data is presented in Table 13. The samples were then hydrated in DI water at 35° and the measurements were performed again. EWC data are presented in Table 14.

TABLE 13

| | RI, Dry 25° C. | | | RI, Dry 35° C. | | | RI, Hydrated 35° C. | | |
|---|---|---|---|---|---|---|---|---|---|
| Sample | Rep 1 | Rep 2 | Avg | Rep 1 | Rep 2 | Avg | Rep 1 | Rep 2 | Avg |
| 230-1 | 1.4748 | 1.4759 | 1.4754 | 1.4722 | 1.4718 | 1.4720 | 1.4702 | 1.4710 | 1.4706 |
| 230-2 | 1.4752 | 1.4755 | 1.4754 | 1.4720 | 1.4721 | 1.4721 | 1.4702 | 1.4712 | 1.4707 |
| 230-3 | 1.4750 | 1.4745 | 1.4748 | 1.4718 | 1.4715 | 1.4717 | 1.4710 | 1.4708 | 1.4709 |
| | Average | Std Dev | | Average | Std Dev | | Average | Std Dev | |
| | 1.4752 | 0.0005 | | 1.4719 | 0.0002 | | 1.4709 | 0.0002 | |

TABLE 14

| | Weights | | | % H$_2$O | |
|---|---|---|---|---|---|
| Sample | Dry | 3 days | 5 days | 3 days | 5 days |
| 230b-1 | 0.0236 | 0.0240 | 0.0240 | 1.67% | 1.67% |
| 230b-2 | 0.0240 | 0.0244 | 0.0244 | 1.64% | 1.64% |
| 230b-3 | 0.0236 | 0.0240 | 0.0240 | 1.67% | 1.67% |
| Average | | | | 1.66% | 1.66% |
| Std. Dev. | | | | 0.02% | 0.02% |

Weight Loss by Exhaustive Extraction of Formulations 214, 215, 218, 219, and 230b Polymer coupons were run through and an in process extraction under the following parameters. The samples were vacuum dried at 60° C. and −40 torr for 72 hours. The mass of six coupons for formulations 214, 215, 218, and 219 were measured, and the mass of ten coupons from two different polymer batches for 230b were measured. The coupons were placed in Acetonitrile and maintained at 35° C. for 72 hours. Coupons were then removed from the Acetonitrile and allowed to air dry for 8 hours. Following the air dry the samples were dried in a vacuum oven for 72 hours. Following the in process extraction an exhaustive extraction in acetonitrile was performed. The mass loss results of the exhaustive extraction are reported in Table 15.

TABLE 15

| Formulation | Average Mass Loss (n = 6) |
|---|---|
| SMP214 | 0.73% ± 0.11 |
| SMP215 | 0.73% ± 0.14 |
| SMP218 | 0.83% ± 0.06 |
| SMP219 | 0.81% ± 0.09 |
| | Average Mass Loss (n = 10) |
| SMP230b | 0.22% ± 0.06 |

Glistening of Formulations 214, 215, 218, 219, and 230b

Coupons were placed in distilled water and maintained at a temperature of 50° C. for 72 hours. The coupons of each formulation were removed from the DI water and inspected under a stereo microscope. Magnifications of 10-80× were used. The entire coupon was analyzed on both sides as well as at various angles to ensure complete inspection of each sample. Table 16 shows that formulations 214, 215, 218, 219, and 230b exhibited no glistening.

TABLE 16

| Formulation | Glistening Observation |
|---|---|
| SMP214 | no glistening |
| SMP215 | no glistening |
| SMP218 | no glistening |
| SMP219 | no glistening |
| SMP230b | no glistening |

Cytotoxicity of Formulations 214, 215, 218, 219, and 230b

Rectangular samples were extracted in acetonitrile as described above. Samples totaling a mass of 4 g were sent out for cytotoxicity testing with a specified extraction ration of 4 g/20 ml.

Based on the foregoing, in certain embodiments, exemplary shape memory polymers as disclosed herein may be derived from tertbutyl acrylate (tBA), one or more PEGDMA monomers (e.g., PEGDMA 1000), one or more UV-blockers, one or more initiators (photo and/or thermal), optionally n-butyl acrylate (nBA), and optionally 2-hydroxy-3-phenoxypropyl acrylate (HPPA).

Optionally, one formulation may target a glass transition temperature (Tg) near body temperature (34-38° C.); and a second formulation may target a lower glass transition temperature (<13° C.). The formulations may form a crosslinked high molecular weight polymer via free radical polymerization. The mode of polymerization may be photochemical, thermal or a combination of both modes of initiation.

The monomers used for these exemplary formulations are listed in Table 17.

TABLE 17

| Monomer | CAS # | Purpose | Approximate Range (wt %) | High Tg Nominal (wt %) | Low Tg Nominal (wt %) |
|---|---|---|---|---|---|
| tert-Butyl Acrylate | 1663-39-4 | Shape Memory | 50-85% | 71.80% | 59.80% |
| n-Butyl Acrylate | 141-32-2 | Modify Tg | 0-20% | 0.0% | 12.00% |
| 2-hydroxy-3-phenoxypropyl acrylate | 16969-10-1 | Increase Refractive Index | 0-20% | 17.50% | 17.50% |
| PEGDMA | 25852-47-5 | Cross-linker | 3-25% | 10.00% | 10.00% |
| UV Blockers | Various | UV-Blocker | 0.25-1.5% | 0.70% | 0.70% |
| Initiator | Various | Polymerization Initiator | 0.05-3.0% | 0.15% | 0.15% |

Higher Tg formulations 235 and 236, as shown in Table 18, were prepared to facilitate the ability to remain compressed at operating room temperature and have a controlled deployment upon introduction into the eye.

TABLE 18

| ID | Formulation |
|---|---|
| SMP235 | tBA(71.8%):HPPA(17.5%):UVB(0.70%):PEGDMA1000(10%):Lauroyl Peroxide(0.15%) |
| SMP236 | tBA(66.8%):HPPA(17.5%):UVB(0.70%):PEGDMA1000(10%):PEGDMA750(5.00%):Lauroyl Peroxide(0.15%) |

Intraocular Lenses

SMP intraocluar lenses are designed to be inserted through significantly smaller incisions than other currently commercially available foldable lens technologies. An exemplary SMP intraocular lens 100 is depicted in FIGS. 1 and 2 and will be discussed in greater detail herein below. In addition the lens shape is highly conserved (i.e., there is high shape fixity >98%) after deployment in the eye. An intracapsular bag lens may have a shape that creates contact with the anterior capsular leaflet as well as the capsule just posterior to the equator allowing for a decrease in posterior capsule opacity formation. A ciliary sulcus lens may have a vault which allows it to avoid trauma to the iris. An anterior chamber lens may have an appropriate vault to decrease the risk of pupillary block and decrease the risk of trauma to the anterior chamber angle support structures.

There are many advantages to SMP technology when applied to intraocular lenses. First, the intraocular lens is compressible and deformable. This ability to compress the material and configure it in a small platform allows for smaller incision sizes for delivery. Such SMP lenses, which fit through smaller incisions, offer significant benefit. For example, with cataract surgery there is less astigmatism, quicker recovery, and less trauma to the eye with smaller incisions. Also, with laser technology and improved ultrasound technology, cataract surgery can be performed with smaller incisions; the limiting factor with present options is the larger incision size needed for the replacement lens.

A second advantage to the shape memory polymer technology in intraocular lens is that deployment of the lens uses thermomechanical recovery rather than an elastic recovery process. The formulation can be modified to change the time or speed of deployment of the lens. This can vary depending upon the location of needed deployment. For example, deployment near delicate structures, such as in the capsular bag or near the corneal endothelium, may require slower, surgeon-tailored deployment to avoid damage to these structures. This modification of deployment speed is not possible with other currently available lens technologies. Also the modulus of the SMP material can be modified to optimize the softness of lens material to minimize trauma to eye structures. For each of the lens types described above, the SMP material properties allow for a slow, tailored deployment, which results in less trauma to the areas with which the lens optic or haptics come in contact.

A third advantage is the ability to easily modify the refractive index of the lens. The refractive index can be changed through modifications of SMP formulation. In addition, the surface curvature of the lens, which is important in designing optical power, can be modified through the liquid injection molding process or post molding with cutting such as with a laser. Further, the curvature of lens as well as the refractive index of the lens can be modified post implantation with heat, UV, or laser light modification.

Figure 7:
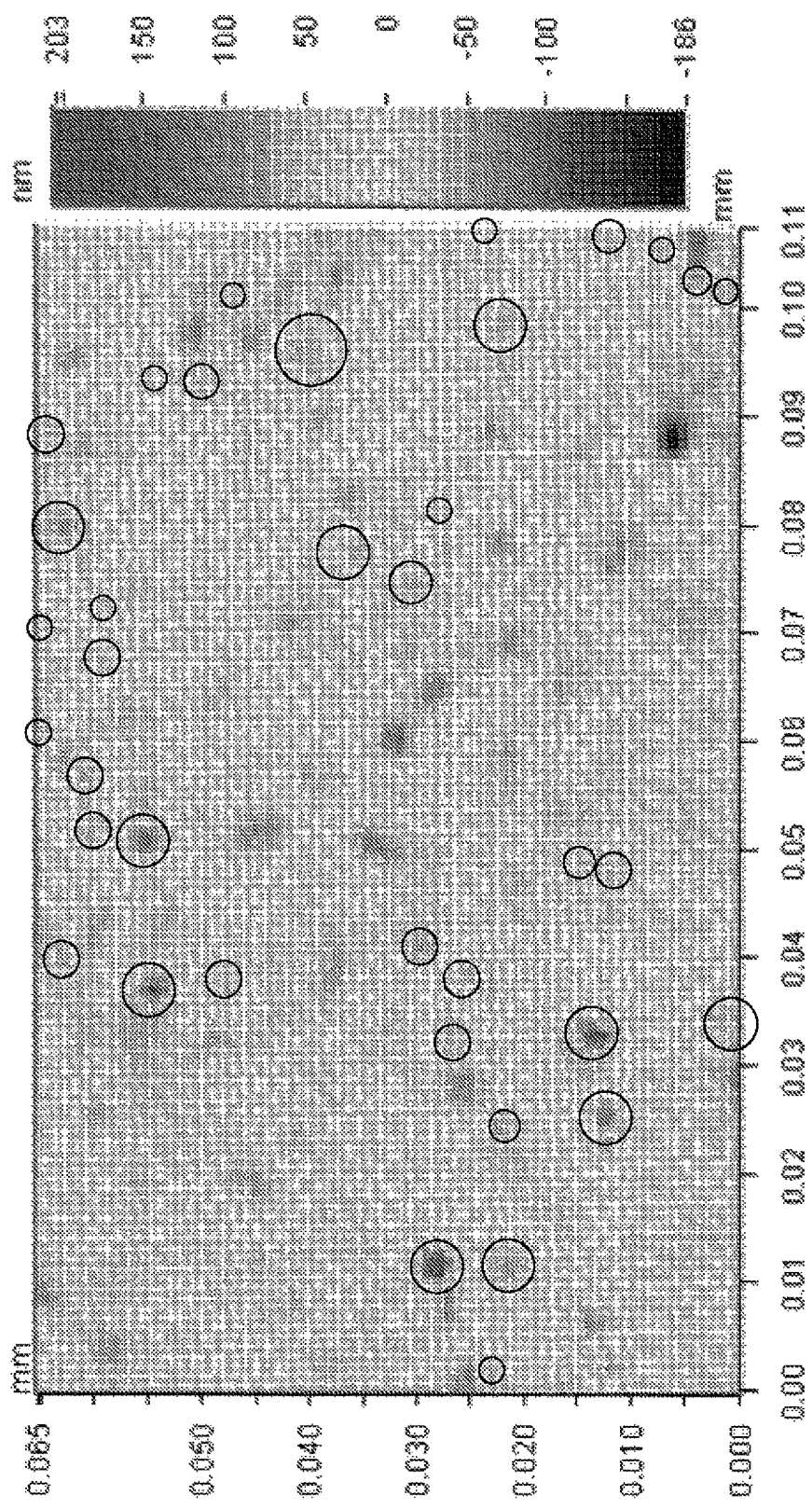
FIG. 7 is an optical profilometry image of a sample SMP IOL lens surface showing average surface roughness.

A fourth advantage is that the surface characteristics and implantation of SMP lenses may decrease inflammation and cellular opacification. As an example, FIG. 7 is an optical profilometry image of a sample SMP lens surface showing average surface roughness of 16 nanometers. This low roughness measure minimizes optical artifacts such as spectral filtering and maximizes optical clarity of the lens. In FIG. 7 the darker areas surrounded by the circles are areas toward the higher end of the measured roughness on the right-hand scale (i.e., toward the 203 nm measurement) while the other dark areas in the image are toward the lower end of measured roughness (i.e., toward the −186 nm measurement). For example, an intracapsular SMP IOL will have contact with the capsular bag to decrease the movement of the lens, but the smoothness of the surface retards the migration of epithelial cells and subsequent formation of posterior capsular opacification.

Since the SMP lens is materially robust, the lenses may be also modified with surface polishing as well as other known mechanisms to reduce the proliferation of cells on the surface of intraocular lenses. In addition the slow deployment of an SMP lens can minimize cellular opacification. There is a tension between the size of the IOL and the collection of epithelial cells on the lens due to the tight fit within the capsular bag. For example, an intracapsular lens will have contact with the capsular bag in a fashion to decrease the migrations of the lens, but the contact with epithelial cells can lead to subsequent formation of posterior capsular opacification, especially if the fit is tight and the material is unable to pass around the lens. This problem is compounded if during deployment, the capsular bag is impacted and damaged, which generates increased cell production in response to the trauma. Configurations of standard intraocular lenses to decrease this common complication of cataract surgery and lens placement are well known. However, with SMP lenses, the size and apposition of the implanted SMP lens to the capsular bag can be increased over current lenses because of the compressibility and deformability of the SMP lens material and the slow deployment that allows a tight fit while minimizing trauma. The ability to polish the surface further mitigates this problem.

Dual Optic Lenses

Larger lenses such as dual optic lenses and other accommodative intraocular lenses may be used to treat refractive error and presbyopia simultaneously. Dual optic lenses are generally constructed with a primary intraocular lens having an optic with a primary optical power and refractive index, and a secondary intraocular lens having an optic with a secondary optical power and possibly a different refractive index. The secondary optic is typically attached to and spaced apart from the primary optic by material struts or similar structures about the periphery of the lenses. The two lenses to act synergistically to allow for both near and distance vision depending on the relationship (e.g., separation distance) between the two optics as well as the geometric association between the two optics which also may (or may not) be adjustable in each individual patient post implantation.

These dual optic lenses often require larger than conventional incisions for entry into the eye. These larger platform lenses may be made with SMP materials, which are highly compressible and deformable allowing for smaller incisions sizes, and thus can improve surgical outcomes for the reasons stated above. In addition, if formed using SMP materials, these larger lenses can be deployed more slowly allowing the surgeon to position the lens in such a fashion as to avoid inadvertent trauma to important eye structures and careful apposition to structures in the target location. This decreases the trauma risk that these larger platform lenses could cause in the eye. In addition, these lenses are quite complex and require high precision optics capabilities, which are conserved because of the high shape fixity of the SMP materials.

Other accommodative lenses strive to replicate the functions of the normal human lens. Mechanisms of accommodation are thought to be secondary to ciliary body contraction and zonular deformation of the lens capsule and a change in lens shape as well as an anterior-posterior movement of the lens complex. With SMP materials, a lens may be created which has close apposition to the lens capsule in multiple areas so that there is an ability to replicate the actions of the native lens. In fact, an SMP lens may be made which expands in the intracapsular space, fills either the whole space or a larger area of the space, and responds to the ciliary body-zonule actions. In addition, an SMP lens can be inserted through a smaller anterior capsular opening, which may help preserve the responsiveness of the lens to the native accommodative process. The local dimensions, thickness in particular, of the SMP lens may be modified post implantation (which may affect local stiffness) if a change in shape is needed to replicate the accommodation process by adding SMP material into the IOL that is of different cross-link density and therefore different activation temperature (Tg) and/or different modulus.

Phakic Intraocular Lenses

A phakic intraocular lens is a lens which is placed in the anterior chamber through a corneal incision. As with the other intraocular lenses discussed above, an SMP phakic lens may be compressed for implantation through a much smaller incision than presently available lenses. A SMP phakic lens may also be designed to deploy slowly so there is little to no corneal endothelial or native lens trauma. The tailored surgeon-controlled deployment allows for positioning of the haptics against the anterior chamber structures without damaging the trabecular meshwork or iris. The force placed on the angle structures by the haptics is consistent and more reproducible than with a conventional lens, which deploys by elastic recovery. A SMP phakic lens may also be designed to deploy in the anterior chamber for placement behind the iris plane during deployment. With current phakic IOL technology, if placed behind the iris, there is a known higher incidence of cataract formation. This incidence can be reduced or eliminated with slow tailored deployment and positioning of an SMP lens.

Intracorneal Implants

Intracorneal implant devices have not achieved great success in the national and international markets due to several limitations which include: (a) difficulty with implantation; (b) requirement for large incisions in the cornea to accommodate current devices; (c) inability to correct "refractive surprises" without returning to the procedure or operating room; and (d) limitation in geometrical configurations of current devices due to inherent material properties. In contrast, SMP intracorneal implants may be designed to leverage the benefits of the compressibility and deformability of SMP materials. A laser or blade is used to make an intracorneal incision, tunnel, and pocket to deliver the intracorneal implant. One of the current challenges is the severe trauma often seen to the corneal tissues during insertion of these devices. A "tight fit" is needed as well as an adequate intracorneal passageway to advance the intracorneal implant. The intracorneal implants are designed to be small enough to atraumatically be passed through a corneal incision and into the desired pocket. Then, the thermomechanical deployment and decompression of the implant occurs allowing for a secure positioning of the implant.

Extrusion and displacement of the intracorneal implants may be decreased with the SMP technology as well as decreasing infection rates because of the minimization of corneal trauma as well as the presence of a smaller incision, tunnel, and pocket. Advantages of using SMP materials for intracorneal implants compared to traditional devices may include the ability to implant devices through minimally invasive approaches (e.g., through incisions created by femtosecond lasers) with subsequent shape change achieving larger device diameters for refractive correction. Another advantage is the ability to change the shape and size of SMP intracorneal implant devices post implantation in the cornea, for example, if a "refractive surprise" occurs or if further changes in refractive correction are needed. This can be achieved by constructing the intracorneal implants with different material formulas in different areas to provide differing Tg and refractive index values for each of the areas as described above with respect to SMP IOLs. A further advantage is the ability to implant the devices in a more "rubbery" state, thus causing less trauma to the stromal tissue of the cornea.

Shape Memory Polymer Intraocular Compression and Packaging

FIGS. 8A-13 depict exemplary steps in a process to deform a SMP IOL into a compressed shape for packaging and implantation, at which point the SMP IOL will deploy and expand to return to its permanent shape with an extremely high degree of shape fixity. FIGS. 8A and 8D depict an exemplary, generic SMP intraocular lens 100. The SMP IOL 100 has a center optic 102 and haptics 104 extending symmetrically from opposing sides of the optic 102. Each of the haptics 104 may be formed in sections including a shoulder 106 connected with the optic 102, an arm 108, and a terminal end 110. Upon deployment, the haptics 104 unfurl from their rolled and compressed conditions to press the terminal ends 110 against the tissue forming the cavity of implantation to secure the optic in an appropriate position.

The SMP IOL is formed by injection molding one of the formulations described above. In an exemplary implementation, an 80-20 (tBA-PEGDMA 550) combination is used to create a 6 min diameter optic 102 with extending haptics 104. The tBA-PEGDMA 550 mixture has extremely low viscosity when heated in the mold and is thus able to easily flow through and fill the mold to form the very small diameter haptics 104. In another exemplary implementation, a combination of tBA (78%) and PEGDMA 1000 (22%), with or without a UV blocker BTA (0.5-1.0%) (e.g., SMP106, SMP122, and SMP123, respectively) may be used to create the optic 100. These formulas similarly have extremely low viscosities. In a cast process molding, the mold may be oversized by 0.1-20% to account for a 5-20% volume shrinkage that typically occurs for these polymer chemistries during the polymerization process. In a liquid injection molding process, ultra-high pressures (e.g., >500-40,000 psi) may be utilized to minimize volume shrinkage as much as possible during polymerization. In addition, the combination of injection molding with pre-polymization techniques may be implemented to further minimize volume shrinkage during the polymerization process.

In one implementation, the cure temperature and de-molding temperature may be the same to avoid thermal cycling. Alternatively, the mold may be cooled to an optimal de-mold temperature where the material exhibits the greatest robustness, typically somewhere slightly (e.g., 8° C.) below Tg. Once released from the mold, the SMP IOL 100 is in its permanent form. However, for implantation, it is desirable to reduce the size and form factor of the SMP IOL 100 such that it can be implanted through a smaller incision.

Figure 9A:
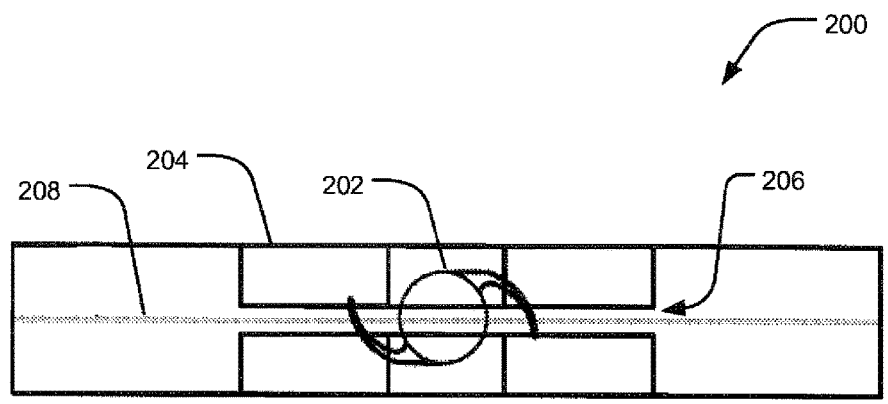
FIG. 9A is a top plan view of an exemplary SMP IOL placed on a rolling die with a channel for rolling the SMP IOL.
Figure 9B:
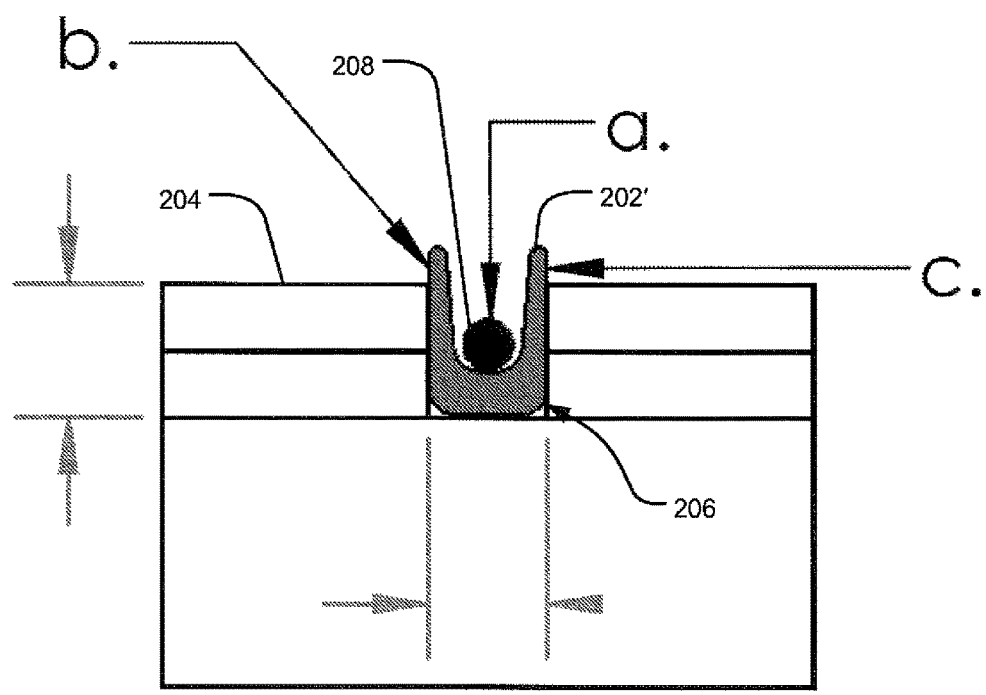
FIG. 9B is a front elevation view of the rolling die of FIG. 2A with the SMP IOL folded into the channel under compression by a wire running axially down the channel.

FIGS. 9A and 9B schematically depict a first step in the deformation process for the SMP IOL 202 to package the SMP IOL 202 into a deformed shape for storage and ultimately implantation. A rolling die 204 defining a longitudinal channel 206 therein may be used to initially roll the SMP IOL 202. The SMP IOL 202 is placed over the channel oriented with the haptics extending across the channel as well. A tension wire 208 is placed parallel to and directly above the channel 206 over the SMP IOL 202 while the ends of the tension wire 208 are position coaxially with the longitudinal center of the channel 206. The rolling die 204 and SMP IOL 202 are then heated to approximately Tg. The tension on the wire 208 is increased, drawing the entire length of the tension wire 208 into the channel 206 the tension wire is coaxial with the longitudinal center of the channel. The tension wire 208 thereby pushes the SMP IOL 202 within the channel 206, folding the SMP IOL 202 in half around the tension wire 208 and deforming the SMP IOL 202 into a U-shape 202' as shown in FIG. 9B. A first side of the U-shaped SMP IOL 202' (labeled "b" in FIG. 213) is folded over the wire 208 in the channel 206. Then a second side of the U-shaped SMP IOL 202' (labeled "c" in FIG. 9B) is folded over the first side about the wire 208. The tension wire 208 can then be removed. In one exemplary embodiment, the channel may be 1.8 mm wide by 2.0 mm deep resulting in an SMP IOL 202' that has maximum diametrical dimensions of 1.8 mm by 2.0 mm.

Figure 10A:
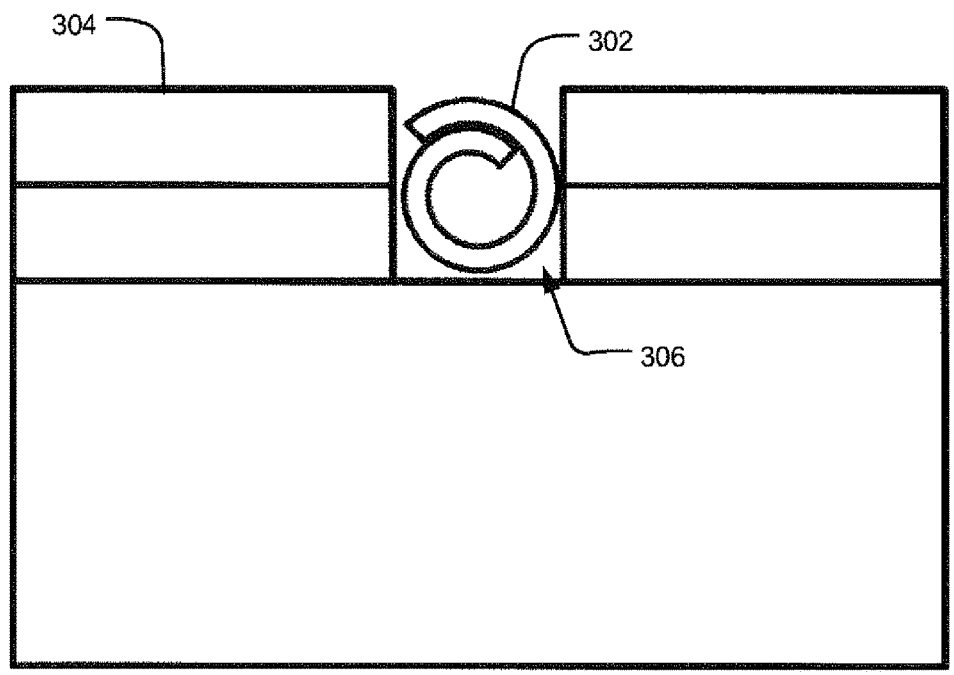
FIG. 10A is a schematic front elevation view of the rolling die of FIG. 2A with the edges of the SMP IOL folded over and the rolling die cooled below Tg.
Figure 10B:
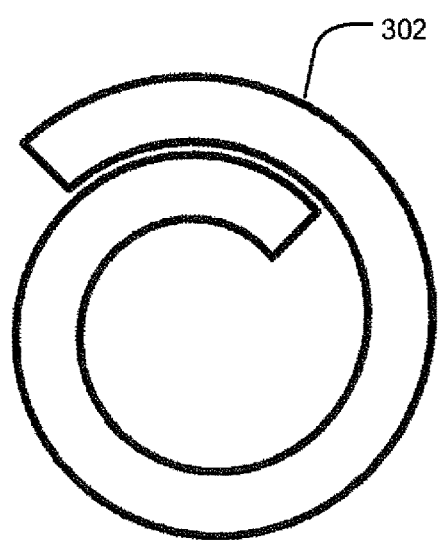
FIG. 10B is a schematic elevation view of the SMP IOL removed from the rolling die and maintaining a deformed, rolled configuration.

As depicted in FIG. 10A, the rolled SMP IOL 302 is next cooled below Tg while remaining within the channel 306 in the rolling die 304. The cooling of the SMP IOL 302 while in the die channel locks the SMP IOL 302 in the rolled configuration. The SMP IOL 302 can then be removed from the channel 306 in the rolling die 304 and will maintain its rolled shape as shown in FIG. 10B.

Figure 11:
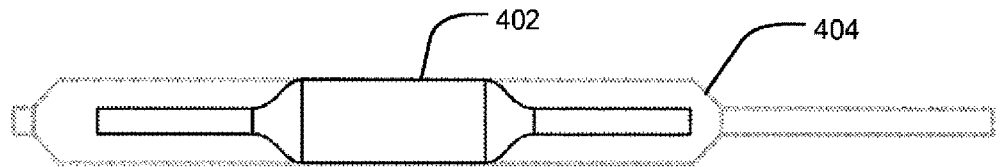
FIG. 11 is a schematic diagram of the rolled SMP IOL placed in a fabric sock.

The rolled SMP IOL 402 is next placed within a fabric sheath or sock 404 as shown in FIG. 11 for transmission of the rolled SMP IOL 402 through a compression die. The fabric sock 404 may be closed at one end and open at an opposite end and sized to fit snugly around the rolled SMP IOL 402. The fabric sock 404 may be significantly longer than the length of the rolled SMP IOL 402 in order to assist in pulling the SMP IOL 402 through a compression die. In an exemplary implementation, the fabric sock 404 may be made of a silk fabric.

Figure 12A:
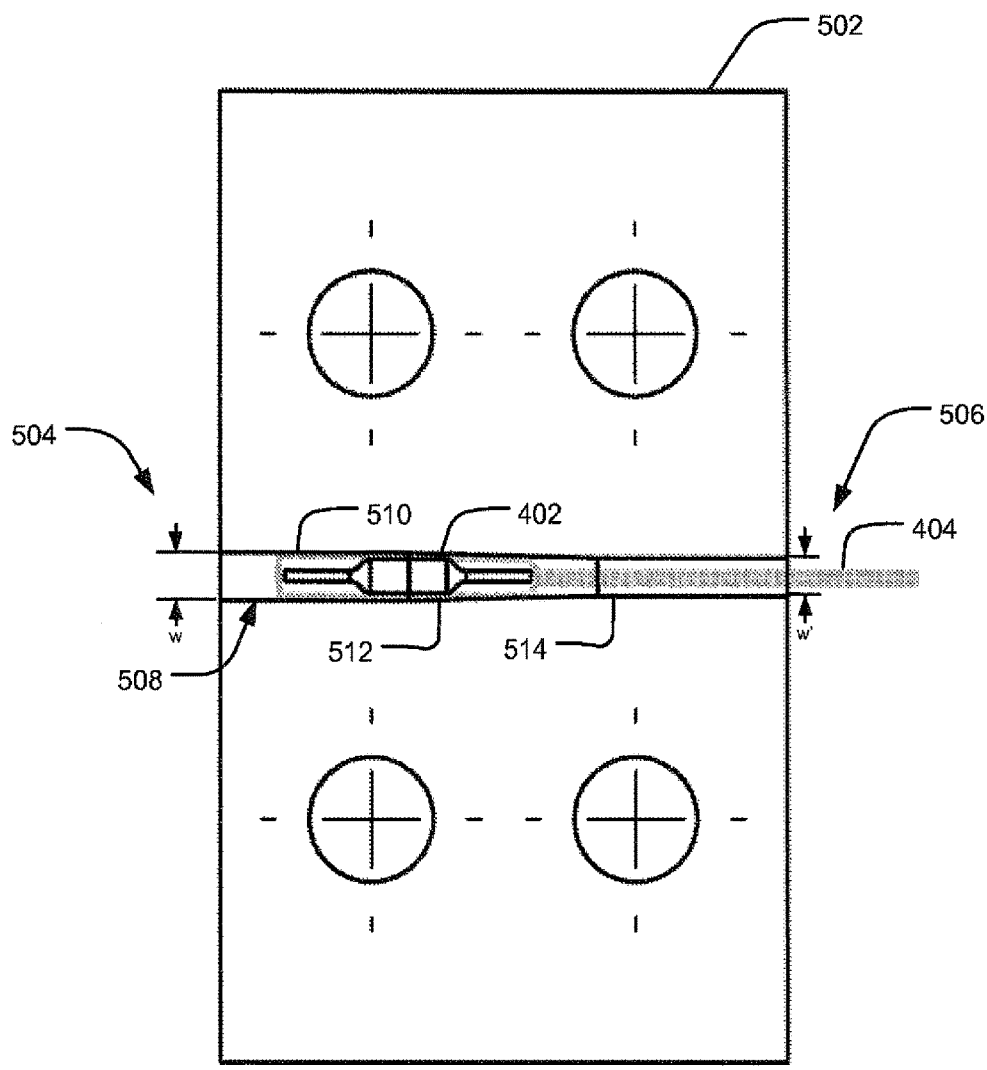
FIG. 12A is a top plan view, in cross section of the SMP IOL within the fabric sock being pulled through a tube of decreasing diameter formed in a compression die heated above Tg.
Figure 12B:
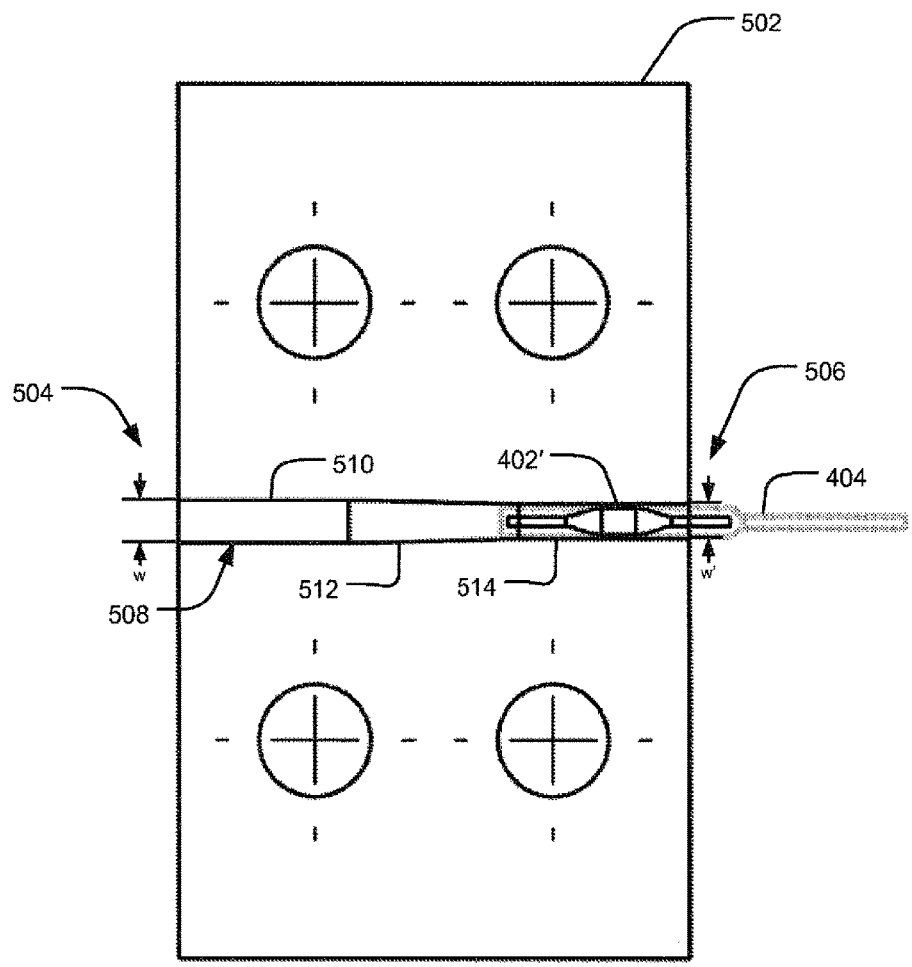
FIG. 12B is a is a top plan view, in cross section of the SMP IOL within the fabric sock compressed within the smallest diameter section of the tube while the compression die is cooled below Tg.

FIGS. 12A and 12B depict the SMP IOL 402 in the fabric sock 404 being pulled through a compression die 502. The compression die 502 defines a borehole 508 extending laterally therethrough from an entrance side 504 to and exit side 506. The borehole 508 in the compression die 502 may be divided into several sections of varying diameter. An entrance section 510 opening up to the entrance side 504 may be of a constant diameter of slightly larger than the diameter of the rolled SMP IOL 402 such that the SMP IOL 402 can be easily inserted into the borehole 508 of the compression die 502. A middle section 512 of the borehole 508 tapers in diameter from the diameter of the entrance section 510 to a smaller diameter that transitions into and is congruent with a diameter of an exit section 514 that opens the exit side 506. Continuing with the exemplary embodiment described above wherein the maximum diameter of the rolled SMP IOL 402 is 2.0 mm, the diameter w of the entrance section 510 may be formed as 2.0 mm or slightly greater. The middle section 512 may then transition from 2.0 mm to 1.5 mm in diameter, and the diameter w' of the exit section may be a constant 1.5 mm in diameter.

Figure 13:
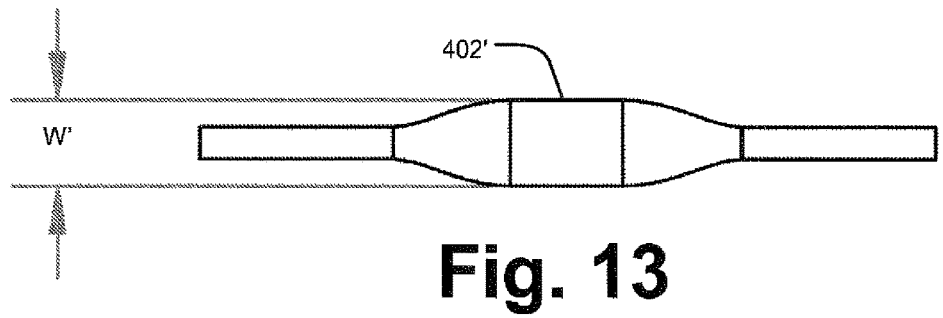
FIG. 13 is a schematic elevation view of the SMP IOL removed from the compression die and sock maintaining a deformed, rolled, extended, and radially compressed configuration.

As shown in FIGS. 12A and 12B, the open end of the fabric sock 404 is placed within the borehole 508 from the entrance side 504 and is long enough to extend the length of the borehole 508 and extend out of the exit side 506. The open end of the fabric sock 404 may then be grasped to pull the rolled SMP IOL 402 within the fabric sock 404 into the entrance section 510 of the borehole 508. The compression die 502 is heated to a temperature greater than Tg for the SMP formulation used until the SMP IOL 402 reaches a temperature greater than Tg and is softened. The fabric sock 404 is then pulled through the borehole 508 whereby the rolled SMP IOL 402 is likewise pulled through the middle section 512 and radially compressed. The compressed SMP IOL 402' is then left in the reduced diameter exit section 514 while the compression die and the compressed SMP IOL 402 therein are cooled to a temperature below Tg, thereby locking the compressed SMP IOL 402' in the compressed state. Once the compressed SMP IOL 402' has been cooled below Tg, it can be removed from the compression die 502 and the fabric sock 404 and will remain in the compressed shape with a maximum diameter of w' for packaging, storage, and ultimately implantation as indicated in FIG. 13.

In an exemplary experiment, an SMP IOL with a 6 mm diameter optic was rolled and compressed to a final diameter, w', of 1.5 mm. The compressed SMP IOL was loaded into a 15 gauge hypodermic tube. The compressed SMP IOL in the tube was then introduced into a heated water bath at body temperature. A rod was inserted within the hypodermic tube to push the IOL out the end of the tube and deliver it into the water bath. Once in the water bath, the SMP IOL expanded and unfurled to return to its original form with a 6 mm diameter optic with >98% accuracy in size and form.

Another exemplary implementation of a device and method for folding the IOL is depicted schematically in FIGS. 14A-14C. FIG. 14A depicts a first step in the deformation process for an SMP IOL 702 to package the SMP IOL 702 into a deformed shape for storage and ultimately implantation. A rolling die 710 is formed with a pair of parallel walls 704 extending above a top surface of the die 710 to define a longitudinal channel 706 therein. The base of the channel 706 may be arcuate or semicircular in cross section in order to aid in the folding and achieve a relatively cylindrical SMP IOL 702 in the final compressed form. The SMP IOL 702 is placed on the walls 704 over the channel 706 and oriented with the haptics extending across the channel 706 as well. The rolling die 710 and SMP IOL 702 are then heated to approximately Tg. The lateral edges of the SMP IOL 702 may then be folded over within the channel 706 between the walls 704 to form a rolled shape similar to the configuration of the IOL 302 in FIG. 10B. In one implementation, the IOL 702 may be folded by hand using a tweezers or forceps. In another implementation, a tension wire as described with respect to FIGS. 9A and 9B may be used to depress the IOL 702 into the channel 706. In one exemplary embodiment, the channel 706 may be 1.8 mm wide by 2.0 mm deep resulting in an SMP IOL 702 that has maximum diametrical dimensions of 1.8 mm by 2.0 mm.

FIG. 14B depicts a second component of the deformation device, a second compression die 720 that works in cooperation with the roll die 710 to further compress the IOL 702. A pair of parallel channels 728 are formed within a top surface of the compression die 720 that are complementary to or slightly larger in size (i.e., length, width, and depth) than the size of the walls 704 (i.e., length, width, and height) of the rolling die 710. A recessed wall 724 is thus formed within the top surface of the compression die 720 that separates and defines the channels 728. The recessed wall 724 may thus be of a complementary width to or slightly smaller in width than the channel 706 on the rolling die 710. The top surface of the recessed wall 724 may further define a shallow trough 726 with a curved or semi-circular cross section. The compression die 720 may further be formed with one or more fluid channels 722 with inlet and outlet fittings in order to maintain the compression die 720 at or above the Tg of the SMP IOL 702.

Once the SMP IOL 702 is rolled in the channel 706 of the rolling die 710, the rolling die 710 is inverted and placed on top of the compression die 720. The walls 704 of the rolling die 710 fit within the channels 728 of the compression die 720. The recessed wall 724 of the compression die 720 extends into the channel 706 of the rolling die 710 and the trough 726 contacts the SMP IOL 702 within the channel 706. The rolling die 710 and the compression die 720 are then pressed together and the SMP IOL 702 is further compressed in size when measured in cross-sectional diameter (however, the SMP IOL may increase in axial length slightly when under radial compression between the rolling die 710 and the compression die 720).

Figure 14:
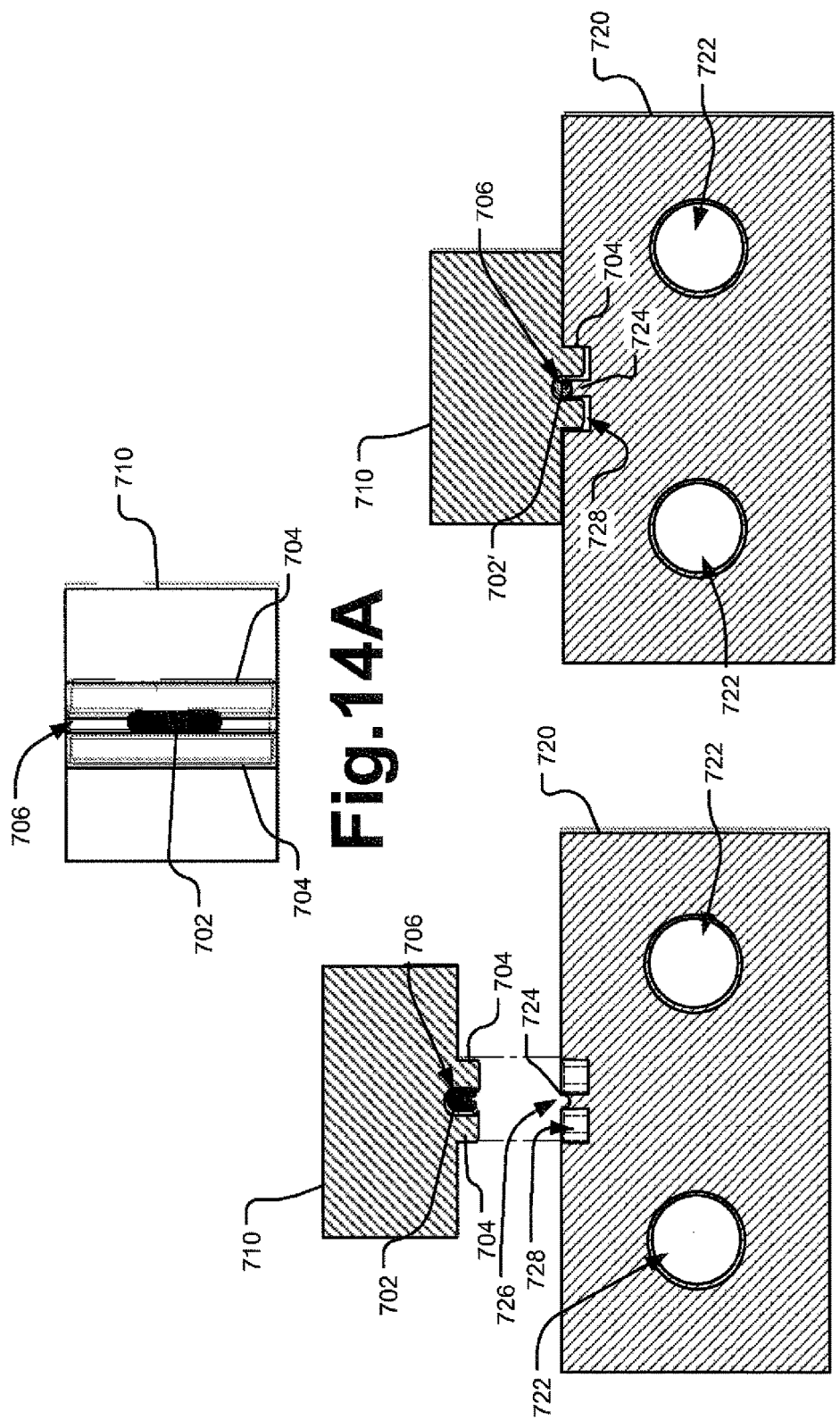
FIG. 14A is a schematic top plan view of a folding and compression tool used to fold a SMP IOL in conjunction with a temperature-regulated compression system.
FIG. 14B is a schematic side elevation view in cross section of the tool of FIG. 7A used in conjunction with a temperature-regulated compression tool.
FIG. 14C is a schematic side elevation view in cross section of the folding and compression tool in a compressed position with the temperature-regulated compression tool.

As shown in FIG. 14 C, since the depth of the parallel channels 728 within the compression die 720 is slightly larger than the height of the parallel walls 704 on the rolling die 710, the top surface of the rolling die 710 and the top surface of the compression die 720 reach an interface and halt the compression of the SMP IOL 702. The depth of the trough 726 and the depth of the channel 706 are chosen to define a separation distance between the base of the channel 706 and the base of the trough 726 that corresponds to a desired final diameter of the compressed SMP IOL 702. In an exemplary experiment, an SMP IOL with a 6 mm diameter optic was compressed using this method to a final diameter of 1.6 mm. The compressed SMP IOL can then be loaded into an injection tool for ab interno delivery.

In another exemplary implementation, an SMP IOL folded by this technique may be loaded into a lens injector for implantation. In an exemplary IOL placement, a small incision may be made at the corneal limbus with a blade or laser and the tip of the injector may be inserted into the anterior chamber. Because of the slow deployment of the SMP IOL, the surgeon can place the haptics and the optic in the correct location during lens deployment to avoid extensive manipulation of the SMP IOL after full deployment. In addition, cataract extraction and lens implantation can be performed with a smaller anterior capsular opening—as small as less than 1.8 mm in diameter. A smaller capsular opening with less disruption of the anterior capsule will increase the accommodative ability of the implanted lens as the physiology of accommodation is less disrupted.

In one exemplary implementation, the injector tip may be placed through the cornea incision, across the anterior chamber, into the small anterior capsular opening. The lens may be injected directly into the capsular bag and slowly deploy without significant trauma to the lens capsule. This is not possible with rapid deployment of known expanding lenses which often leads to capsular tears. Similarly a sulcus SMP IOL will be supported in the ciliary sulcus with gentle pressure and apposition of the haptics to the ciliary sulcus structures. Further, an anterior chamber SMP IOL will be supported by the anterior chamber angle structures with gentle pressure and apposition of the haptics to the anterior chamber angle structures. The slow, gradual deployment of an SMP IOL will significantly reduce the trauma to these tissue structures as compared to the rapid, elastic deployment of present IOL materials.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

What is claimed is:

1. An intraocular lens comprising:
   a refractive index above 1.45;
   a glass transition temperature (Tg) between 10° C. and 60° C., inclusive;
   de minimis or an absence of glistening; and
   substantially 100% transmissivity of light in the visible spectrum,
   wherein the intraocular lens comprises a tert-butyl acrylate (tBA) monomer,
   and wherein the intraocular lens comprises a crosslinking monomer selected from the group consisting of: poly(ethylene glycol) diacrylate with a molecular weight substantially between 500 and 2000, inclusive; and poly(ethylene glycol) dimethacrylate (PEGDMA) with a molecular weight substantially between 500 and 2000, inclusive.

2. The intraocular lens of claim 1, wherein the intraocular lens is formed from a combination of 50 weight percent tert-butyl acrylate monomers, 28 weight percent isobutyl acrylate monomers, and 22 weight percent PEGDMA 1000 crosslinking monomers.

3. The intraocular lens of claim 1, wherein the intraocular lens is formed from a combination of 78 weight percent tert-butyl acrylate monomers and 22 weight percent PEGDMA 1000 crosslinking monomers.

4. The intraocular lens of claim 1, wherein the intraocular lens is formed from a combination of 65 weight percent tert-butyl acrylate monomers, 13 weight percent butyl acrylate monomers, and 22 weight percent PEGDMA 1000 crosslinking monomers.

5. The intraocular lens of claim 1, wherein the crosslinking monomer is PEGDMA 1000.

6. The intraocular lens of claim 1, further comprising a n-butyl acrylate (nBA) monomer.

7. The intraocular lens of claim 1, further comprising a photo-initiator.

8. The intraocular lens of claim 1, further comprising a n-butyl acrylate (nBA) monomer and a photo-initiator, and wherein the crosslinking monomer is PEGDMA 1000.

9. The intraocular lens of claim 1, wherein the intraocular lens has a Tg between 15° C. and 45° C., inclusive.

10. The intraocular lens of claim 8, wherein the intraocular lens has a Tg between 15° C. and 45° C., inclusive.

* * * * *